US008673635B2

(12) United States Patent
Sokal et al.

(10) Patent No.: US 8,673,635 B2
(45) Date of Patent: Mar. 18, 2014

(54) ISOLATED LIVER STEM CELLS

(75) Inventors: Etienne Sokal, Hoeilaart (BE);
Mustapha Najimi, Woluwé
Saint-Lambert (BE)

(73) Assignee: Universite Catholique de Louvain,
Louvain-la-Neuve (BE)

( * ) Notice: Subject to any disclaimer, the term of this patent is extended or adjusted under 35 U.S.C. 154(b) by 1239 days.

(21) Appl. No.: 12/097,743

(22) PCT Filed: Dec. 14, 2006

(86) PCT No.: PCT/EP2006/012046
§ 371 (c)(1),
(2), (4) Date: Jun. 16, 2008

(87) PCT Pub. No.: WO2007/071339
PCT Pub. Date: Jun. 28, 2007

(65) Prior Publication Data
US 2008/0311094 A1 Dec. 18, 2008

(30) Foreign Application Priority Data

Dec. 21, 2005 (EP) ..................................... 05447286
Oct. 17, 2006 (WO) ................. PCT/EP2006/010014

(51) Int. Cl.
*C12N 5/074* (2010.01)
*C12N 5/071* (2010.01)
*C12N 5/00* (2006.01)

(52) U.S. Cl.
USPC ........... 435/370; 435/378; 435/395; 435/402; 424/93.7

(58) Field of Classification Search
USPC .................. 435/370, 378, 395, 402; 424/93.7
See application file for complete search history.

(56) References Cited

U.S. PATENT DOCUMENTS

| 6,242,252 | B1 | 6/2001 | Reid et al. |
| 6,774,120 | B1 | 8/2004 | Ferber |
| 8,119,405 | B2 | 2/2012 | Ferber |
| 2003/0138951 | A1 | 7/2003 | Yin |
| 2004/0213769 | A1 | 10/2004 | Ferber |
| 2005/0074876 | A1 | 4/2005 | Strick-Marchand et al. |
| 2005/0090465 | A1 | 4/2005 | Ferber |
| 2012/0329710 | A1 | 12/2012 | Ferber |

FOREIGN PATENT DOCUMENTS

| WO | WO 94/08598 | | 4/1994 |
| WO | WO 00/72885 | | 12/2000 |
| WO | WO 03/000848 | | 1/2003 |
| WO | WO 2004/098646 | | 11/2004 |
| WO | WO 2006/126236 | * | 5/2006 |
| WO | WO 2006/126219 | * | 11/2006 |
| WO | WO 2006/126236 | | 11/2006 |

OTHER PUBLICATIONS

Azuma, et al. "Enrichment of Hepatic Progenitor Cells from Adult Mouse Liver," *Hepatology*, vol. 37, No. 6, pp. 1385-1394, Jun. 2003.
Herrera, et al. "Isolation and Characterization of a Stem Cell Population from Adult Human Liver," *Stem Cells*, vol. 24, No. 12, pp. 2840-2840, Aug. 2006.
Laurson, et al. "Hepatocyte Progenitors in Man and in Rodents—Multiple Pathways, Multiple Candidates," *International Journal of Experimental Pathology*, vol. 86, No. 1, pp. 1-18, Feb. 2005.
Tateno, et al. "Growth and Differentiation in Culture of Clonogenic Hepatocytes that Express Both Phenotypes of Hepatocytes and Biliary Epithelial Cells," *American Journal of Pathology*, vol. 149, No. 5, pp. 1593-1605, Nov. 1996.
Walkup, et al al. "Hepatic Stem Cells: In Search of," *Stem Cells*, vol. 24, No. 8, pp. 1833-18409, Aug. 2006.
Wang, et al. "Proliferation and Hepatic Differentiation of Adult-Derived Progenitor Cells," *Cells, Tissues, Organs 2003*, vol. 173, No. 4, pp. 193-203, 2003.
International Search Report dated Mar. 14, 2007.
Chagraoui, et al. "Fetal Liver Stroma Consists of Cells in Epithelial-to-Mesenchymal Transition," *Blood*, vol. 101, No. 8, pp. 2973-2982, Apr. 15, 2003.
Dhawan, et al. "Hepatocyte Transplantation for Liver-based Metabolic Disorders," *Journal of Inherited Metabolic Disease*, vol. 29, pp. 431-435, 2006.
Khuu, "In vitro Differentiated Adult Human Liver Progenitor Cells Display Mature Hepatic Metabolic Functions: A Potential Tool for In vitro Pharmaco-toxicological Testing," Final Apr. 2010 compiled, 45 pages.
Kim, et al. "Formation of Vitamin A Lipid Droplets in Pancreatic Stellate Cells Requires Albumin," *Gut*, vol. 58, pp. 1382-1390, 2009.
Lim, et al. "Modulation of Cytokeratin Expression During In vitro Cultivation of Human Hepatic Stellate Cells: Evidence of Transdifferentiation from Epithelial to Mesenchymal Phenotype," *Histochemistry and Cell Biology*, vol. 118, pp. 127-136, 2002.
Najimi, et al. "Adult-derived Human Liver Mesenchymal-like Cells as a Potential Progenitor Reservoir of Hepatocytes?," *Cell Transplantation*, vol. 16, pp. 717-728, 2007.
Piscaglia, et al. "Stem Cell-based Therapies for Liver Diseases: State of the Art and New Perspectives," *Stem Cells International*, SAGE-Hindawi Access to Research, vol. 2010, Article ID 259461, 10 pages, 2010.
Shipp, et al. "Hematopoietic Differentiation Antigens That are Membrane-associated Enzymes: Cutting is the Key!," *Blood*, vol. 82, No. 4, pp. 1052-1070, 1983.
Stutchfield, et al. "Prospects for Stem Cell Transplantation in the Treatment of Hepatic Disease," *Liver Transplantation*, vol. 16, pp. 827-836, 2010.

(Continued)

*Primary Examiner* — Anne Marie S Wehbe
(74) *Attorney, Agent, or Firm* — Knobbe, Martens, Olson & Bear LLP

(57) ABSTRACT

Isolated liver progenitor stem cells and cell populations of isolated liver progenitor stem cells are disclosed. The progenitor stem cells originate from adult liver, especially human adult liver. The isolated progenitor stem cells have uses in medicine, hepatology, inborn errors of liver metabolism transplantation, infectious diseases and liver failure. Methods of isolating these cells and their culture is described. The isolated cells are characterized before and after differentiation. Their use for transplantation and as animal models of human disease, toxicology and pharmacology is disclosed.

18 Claims, 6 Drawing Sheets

(56) References Cited

OTHER PUBLICATIONS

Turner, et al. Human Hepatoblast Phenotype Maintained by Hyaluronan Hydrogels, *Journal of Biomedical Materials Research Part B: Applied Biomaterials*, vol. 82, No. 1, pp. 156-168, Abstract only, Jul. 2007.

Zhang et al., "The existence of epithelial-to-mesenchymal cells with the ability to support hematopoiesis in human fetal liver," *Cell Biology International*, vol. 29(3), pp. 213-219 (Mar. 2005).

Avigdor, et al. "CD44 and Hyaluronic Acid Cooperate with SDF-1 in the Trafficking of Human CD34+ Stem/Progenitor Cells to Bone Marrow," *Blood*, vol. 103, No. 8, pp. 2981-2989, Apr. 15, 2004.

Avital, et al. "Bone Marrow-derived Liver Stem Cell and Mature Hepatocyte Engraftment in Livers Undergoing Rejection," *Surgery*, vol. 132, No. 2, pp. 384-390 Aug. 2002.

Barry, et al. "The SH-3 and SH-4 Antibodies Recognize Distinct Epitopes on CD73 from Human Mesenchymal Stem Cells," *Biochemical and Biophysical Research Communications*, vol. 289, No. 2, pp. 519-524, 2001.

Bartholomew, et al. "Baboon Mesenchymal Stem Cells can be Genetically Modified to Secrete Human Erythropoietin In Vivo," *Human Gene Therapy*, vol. 12, No. 12, pp. 1527-1541, Aug. 10, 2001.

Boiret, et al. "Characterization of Nonexpanded Mesenchymal Progenitor Cells from Normal Adult Human Bone Marrow," *Experimental Hematology*, vol. 33, No. 2, pp. 219-225, Feb. 2005.

Coves, et al. "Mesenchymal Stem Cells can be Obtained from the Human Saphena Vein," *Experimental Cell Research*, vol. 309, No. 2, pp. 240-244, Oct. 1, 2005.

Dabeva, et al. "Differentiation of Pancreatic Epithelial Progenitor Cells into Hepatocytes Following Transplantation into Rat Liver," *PNAS USA*, vol. 94, No. 14, pp. 7356-7361, Jul. 1997.

Di Campli, et al. "A Human Umbilical Cord Stem Cell Rescue Therapy in a Murine Model of Toxic Liver Injury," *Digestive and Liver Disease*, vol. 36, No. 9, pp. 603-613, Sep. 2004.

Dimitroff, et al. "CD44 is a Major E-Selectin Ligand on Human Hematopoietic Progenitor Cells," *Journal of Cell Biology*, vol. 153, No. 6, pp. 1277-1286, Jun. 11, 2001.

Dragoo, et al. "Bone Induction by*BMP-2* Transduced Stem Cells Derived from Human Fat," *Journal of Orthopaedic Research*, vol. 21, No. 4, pp. 622-629, Jul. 2003.

Espinosa-Heidmann, et al. "Bone Marrow-derived Progenitor Cells Contribute to Experimental Choroidal Neovascularizaton," *Investigative Ophthalmology & Visual Science*, vol. 44, No. 11, pp. 4914-4919, Nov. 2003.

Fang, et al. "Systemic Infusion of FLK1+ Meschenchymal Stem Cells Ameliorate Carbon Tetrachloride-induced Liver Fibrosis in Mice," *Transplantation*, vol. 78, No. 1, pp. 83-88, Jul. 15, 2004.

Furnus, et al. "The Hyaluronic Acid Receptor (CD44) is Expressed in Bovine Oocytes and Early Stage Embryos," *Theriogenology*, vol. 60, No. 9, pp. 1633-1644, Dec. 2003.

Haleem-Smith, et al. "Optimization of High-efficiency Transfection of Adult Human Mesenchymal Stem Cells In Vitro," *Molecular Biotechnology*, vol. 30, No. 1, pp. 9-20, May 2005.

Hisatomi, et al. "Flow Cytometric Isolation of Endodermal Progenitors from Mouse Salivary Gland Differentiate into Hepatic and Pancreatic Lineages," *Hepatology*, vol. 39, No. 3, pp. 667-675, Mar. 2004.

Hoppo, et al. "Thy1-positive Mesenchymal Cells Promote the Maturation of CD49f-positive Hepatic Progenitor Cells in the Mouse Fetal Liver," *Hepatology*, vol. 39, No. 5, pp. 1362-1370, 2004.

Igura, et al. "Isolation and Characterization of Mesenchymal Progenitor Cells from Chorionic Villi of Human Placenta," *Cytotherapy*, vol. 6, No. 6, pp. 543-553, 2004.

Jostarndt-Fögen, et al. "Expression of Smooth Muscle Markers in the Developing Murine Lung: Potential Contractile Properties and Lineal Descent," *Histochemistry and Cellular Biology*, vol. 110, No. 3, pp. 273-284, Sep. 1998.

Kicic, et al. "Are Stem Cell Characteristics Altered by Disease State?," *Stem Cells and Development*, vol. 14, No. 1, pp. 15-28, Feb. 2005.

Ko, et al. "Expression of the Intermediate Filament Vimentin in Proliferating Duct Cells as a Marker of Pancreatic Precursor Cells," *Pancreas*, vol. 28, No. 2, pp. 121-128, Mar. 2004.

Kwon, et al. "Cellular Manipulation of Human Embryonic Stem Cells by TAT-PDX1 Protein Transduction," *Molecular Therapy*, vol. 12, No. 1, pp. 28-32, Jul. 2005.

Lange, et al. "Liver-specific Gene Expression in Mesenchymal Stem Cells is Induced by Liver Cells," *World Journal of Gastroenterology*, vol. 11, No. 29, pp. 4497-4504, Aug. 7, 2005.

Lázaro, et al. "Generation of Hepatocytes from Oval Cell Precursors in Culture," *Cancer Research*, vol. 58, No. 23, pp. 5514-5522, Dec. 1, 1998.

Lee, et al. "Human Mesenchymal Stem Cells Maintain Transgene Expression during Expansion and Differentiation," *Molecular Therapy*, vol. 3, No. 6, pp. 857-866, Jun. 2001.

Lee, et al. "Mesenchymal Stem Cells from Cryopreserved Human Umbilical Cord Blood," *Biochemical and Biophysical Research Communications*, vol. 320, No. 1, pp. 273-278, Jul. 2004.

McGuckin, et al. "Production of Stem Cells with Embryonic Characteristics from Human Umbilical Cord Blood," *Cell Proliferation*, vol. 38, No. 4, pp. 245-255, Aug. 2005.

Marx, et al. "High-efficiency Transduction and Long-term Gene Expression with a Murine Stem Cell Retroviral Vector Encoding the Green Fluorescent Protein in Human Marrow Stromal Cells," *Human Gene Therapy*, vol. 10, No. 7, pp. 1163-1173, May 1, 1999.

Milbrandt, et al. "Tracing Transduced Cells in Osteochondral Defects," *Journal of Pediatric Orthopaedics*, vol. 23, No. 4, pp. 430-436, Jul.-Aug. 2003.

Nava, et al. "Characterization of Cells in the Developing Human Liver," *Differentiation*, vol. 73, No. 5, pp. 249-260, Jun. 2005.

Oshima, et al. "Behavior of Transplanted Bone Marrow-derived GFP Mesenchymal Cells in Osteochondral Defect as a Simulation of Autologous Transplantation," *Journal of Histochemistry & Cytochemistry*, vol. 53, No. 2, pp. 207-216, Feb. 2005.

Panepucci, et al. "Comparison of Gene Expression of Umbilical Cord Vein and Bone Marrow-derived Mesenchymal Stem Cells," *Stem Cells*, vol. 22, No. 7, pp. 1263-1278, 2004.

Sabatini, et al. "Human Bronchial Fibroblasts Exhibit a Mesenchymal Stem Cell Phenotype and Multilineage Differentiating Potentialities," *Laboratory Investigation*, vol. 85, No. 8, pp. 962-971, Aug. 2005.

Sarugaser, et al. "Human Umbilical Cord Perivascular (HUCPV) Cells: A Source of Mesenchymal Progenitors," *Stem Cells*, vol. 23, No. 2, pp. 220-229, Feb. 2005.

Schwartz, et al. "Multipotent Adult Progenitor Cells from Bone Marrow Differentiate into Functional Hepatocyte-like Cells," *The Journal of Clinical Investigation*, vol. 109, No. 10, pp. 1291-1302, May 2002.

Shi, et al. "Perivascular Niche of Postnatal Mesenchymal Stem Cells in Human Bone Marrow and Dental Pulp," *Journal of Bone and Mineral Research*, vol. 18, No. 4, pp. 696-704, Apr. 2003.

Shiojiri, et al. "Cell Lineages and Oval Cell Progenitors in Rat Liver Development," *Cancer Research*, vol. 51, No. 10, pp. 2611-2620, May 15, 1991.

Totsugawa, et al. "Lentiviral Transfer of the LacZ Gene into Human Endothelial Cells and Human Bone Marrow Mesenchymal Stem Cells," *Cell Transplantation*, vol. 11, No. 5, pp. 481-488, 2002.

Wang, et al. "Mesenchymal Stem Cells in the Wharton's Jelly of the Human Umbilical Cord," *Stem Cells*, vol. 22, No. 7, pp. 1330-1337, 2004.

Wang, et al. "Expression of Hepatocyte-like Phenotypes in Bone Marrow Stromal Cells after HGF Induction," *Biochemical and Biophysical Research Communications*, vol. 320, No. 3, pp. 712-716, Jul. 30, 2004.

Yamamoto, et al. "A Subpopulation of Bone Marrow Cells Depleted by a Novel Antibody, Anti-Liv8, is Useful for Cell Therapy to Repair Damaged Liver," *Biochemical and Biophysical Research Communications*, vol. 313, No. 4, pp. 1110-1118, Jan. 23, 2004.

Ferber et al., "Pancreatic and duodenal homeobox gene 1 induces expression of insulin genes in liver and ameliorates streptozotocin-induced hyperglycemia," *Nature Medicine*, vol. 6(5), pp. 568-572 (May 2000).

(56) References Cited

OTHER PUBLICATIONS

Kim et al., "Functional Human Hepatocytes: Isolation from Small Liver Biopsy Samples and Primary Cultivation with Liver-specific Functions," *The Journal of Toxicological Sciences*, vol. 20(5), pp. 565578 (1995).

Meivar-Levy et al., "New organs from our own tissues: liver-to-pancreas transdifferentiation," TRENDS in Endocrinology and Metabolism, vol. 14(10), pp. 460-466 (Dec. 2003).

Meivar-Levy et al., "Regenerative Medicine: Using Liver to Generate Pancreas for Treating Diabetes," *IMAJ*, vol. 8(6), pp. 430-434 (Jun. 2006).

Naughton et al., "A Stereotypic, Transplantable Liver Tissue-Culture System," Applied Biochemistry and Biotechnology, vol. 54, pp. 65-91 (1995).

Sapir et al., "Cell-replacement therapy for diabetes: Generating functional insulin-producing tissue from adult human liver cells," *Proc Natl Aced Sci.*, vol. 102(22), pp. 7964-7969 (May 31, 2005).

\* cited by examiner

ISOLATED LIVER STEM CELLS

CROSS-REFERENCE TO RELATED APPLICATIONS

This application is the U.S. National Phase under 35 U.S.C. §371 of International Application PCT/EP2006/012046, filed Dec. 14, 2006, which claims priority to PCT/EP2006/10014 filed Oct. 17, 2006 and EP 05447286.5, filed Dec. 21, 2005.

FIELD OF THE INVENTION

The present invention relates to isolated liver progenitor or stem cells, originated from adult liver, and to their use in medicine, hepatology, inborn errors of liver metabolism, transplantation, infectious diseases, liver failure. The present invention also relates to methods of isolating these cells, their culture, characterization before and after differentiation, and their use for transplantation, animal models of human disease, artificial organ devices, toxicology and pharmacology.

BACKGROUND OF THE INVENTION

Liver is a key organ performing many vital functions such as glucose homeostasis, xenobiotic detoxification or macromolecule synthesis. Hence, impairment of one of the multiple liver functions could have a dramatic impact on health. Worldwide incidence of acute or chronic liver diseases sets these pathologies between the 5th and the 9th cause of death, according to the World Health Organization. So far, the only curative treatment for end-stage liver disease remains liver transplantation. The outcome for patients who went through surgical liver replacement is rather good; with more than 95% of recovery. However, despite new surgical techniques, including split-liver and living-related donor, the increasing organ shortage leads to higher mortality on the waiting list. Therefore, an important goal in transplantation medicine research is the demonstration of potential use of liver cells in liver regeneration and treatment of hepatic diseases.

Liver cell transplantation (LCT) is an emerging procedure, involving the infusion of liver cell suspension in the portal system of the recipient. It aims to a recovery of the recipient's liver function as a consequence of engraftment and repopulation of the diseased parenchyma. LCT was first validated in animal models in which syngeneic hepatocytes have been shown to survive indefinitely and be able to correct various enzyme defects (for review, see Najimi and Sokal. 2005. Minerva Pediatr 57(5): 243-57).

In human, early studies were designed for the treatment of acute liver failure. These studies prompted clinicians to extend LCT to further indications and so far at least thirty cases have been reported worldwide for various defects (Strom et al., 1997. Transplant Proc 29(4): 2103-6). In the specific field of metabolic diseases, thirteen cases reported the use of hepatocytes, for the treatment of, among others, Crigler-Najjar syndrome type I, urea cycle defects or rare diseases, such as, e.g., infantile Refsum's disease. These studies demonstrated the engraftment of hepatocytes within the parenchyma and consequently an improvement of the patient status up to 18 months post-transplantation.

However, because supply of mature human hepatocytes for transplantation is still limited, in fact more or less as limited as the availability of whole liver, research also aims at obtaining transplantable cells from other sources, such as progenitor and stem cells, e.g., of embryonic or adult origin, that could be expandable, e.g., in vitro, and able to differentiate into functional mature hepatocytes, esp. in vivo after transplantation. Accordingly, there is a great need to develop new means that are useful in treating various diseases or conditions associated with liver associated diseases, particularly given the inadequate treatments currently available for the majority of these disorders.

Historically, embryonic stem (ES) cells were thought to be involved only in the organogenesis, due to their observed unlimited clonal division and pluripotent differentiation into daughter cells of entire tissues. On the other hand, regeneration processes in adult organs were typically ascribed to adult progenitor cells. Nevertheless, this theory has been revised in view of the discovery in adult organs of stem cells expressing known embryonic markers. Hence, characterisations of stem and progenitor cells are now based not only on the development process (embryonic versus adult), but also on the presence of specific cellular markers therein. Indeed, expression of cellular markers, such as membrane proteins or transcription factors, may vary along the differentiation pathways and reflect various stimuli (e.g., environmental stimuli) and cellular needs. Often, it is observed that in the course of a differentiation process, a stem cell will gradually cease to display markers indicative of its pluripotence, e.g., Oct-4, and being to express markers attributable to later stages, e.g., markers of a specific lineage. As a non-limiting example, Oct-4 may be progressively lost through maturation and, on the other hand, cells entering the endodermal lineage may begin to express alpha-fetoprotein.

Concerning liver regeneration through cell transplantation, several possible source cell types may be considered. For example, ES cells would be expected to be capable of regenerating any organ, due to their pluripotence. Indeed, this avenue is extensively explored in the art. However, ES cells are prone to generate tumour growth when introduced in any other tissue than in utero. Therefore, their use in vivo remains limited by the risk of carcinogenic deviation. Even successful prior in vitro differentiation of ES cells might not be safe enough to consider human inoculation.

A safer alternative would be the use of adult progenitor cells which, unlike ES cells, tend to display limited capacity for clonal division and their differentiation give rise to daughter cells with more limited fates. In liver, adult progenitors such as oval cells (cholangiocytes and hepatocytes precursors) or small hepatocyte-like cells have been described. However, their medical use is rendered difficult by their scarcity in normal adult organs.

Consequently, adult stem cells that would show capability of clonal division with reduced or absent risk of carcinogenic deviation would represent a great improvement in cell transplantation sources. Several types of adult stem cells are currently being evaluated in liver cell transplantation studies. For example, mesenchymal stem cells (MSC) from peripheral or umbilical cord blood are being studied due to their ability to trans-differentiate into more mature cells from another lineage. Moreover, hematopoietic stem cells from marrow have also been studied in terms of liver regeneration potencies.

While in vitro characterization of adult stem cells still presents difficulties, it is currently accepted in the field that such characterisation may advantageously involve detecting (i) markers of its embryonic origin or lineage (esp., mesodermal, endodermal, ectodermal or hematopoietic), (ii) expression of markers reflecting the level of differentiation and thus to some degree predictive of the different possible progenies and, (iii) in vitro or in vivo fate after differentiation. Consequently, characterisation and distinguishing of adult stem cells obtainable from normal liver may advantageously involve evaluation of the presence or absence of (i) marker(s) reflecting the complex embryonic origin of this organ, (ii)

marker(s) of differentiation (e.g., presence of albumin) and, (iii) at least one marker indicative of the stem cell fate.

According to current knowledge, liver originates mainly from the endoderm and hepatocytes are part of the endodermal lineage. However, the formation of the hepatic cells also involves the interaction between the endodermal epithelium and the cardiogenic mesoderm. Furthermore, in foetal development haematopoiesis also takes place in the liver. Given this interplay during development, one needs to be open minded when contemplating markers present in adult liver stem cells, since markers of the endodermal, mesodermal and/or haematopoietic lineages might be expected.

When assessing the differentiation level and cell type commitment, different cell markers may be evaluated, as carried out further in this disclosure. For example, during the differentiation process of cells some markers may decrease or disappear, others may increase or may be gained, and yet others may be maintained all way to a specialised and functional cell. By virtue of non-limiting example, during organogenesis, i.e. during foetal life, hepatoblasts are considered to be the common progenitors of cells forming the parenchyma (esp. hepatocytes and biliary cells) and express inter alia cytokeratin-7 (CK-7) as well as CK-19, albumin and α-fetoprotein. In adult liver, a known common progenitor for hepatocytes and biliary cells is the oval cell, that expresses CK-19, albumin and α-fetoprotein. After differentiation into biliary cells, expression of CK-19 and α-fetoprotein is maintained while expression of CK-7 (considered a feature of more immature cells) tends to cease. On the other hand, hepatocytes maintain expression of α-fetoprotein and albumin, but do not show expression of the above CK. Also from this example, it follows that stem cell characterization may be complex, but that the assessment of markers may be advantageously used to indicate the cells' type or properties.

To the inventors' knowledge, previous studies described the isolation of progenitor cells from normal adult liver, which cells demonstrated more than one cell fate. An adult liver stem cell line capable of in vitro amplification and in vivo differentiation into hepatocytes, and preferably with only the hepatocytic cell fate has not been described. Moreover, previous studies used complicated techniques, such as FACS, calcium-implemented media or specific density gradients to isolate their liver stem cells.

Accordingly, it is an object of the invention to provide novel adult liver derived progenitor or stem cells with improved properties, and particularly useful in, e.g., liver cell transplantation. The invention also sets out to provide a simple method to isolate the said cells.

SUMMARY OF THE INVENTION

The invention provides adult liver derived progenitor or stem cells, cell lines thereof or cell populations comprising such, obtained from a normal liver tissue. Methods of isolating these cells, their culture, characterization before and after differentiation, and their use for transplantation, animal models of human disease, toxicology and pharmacology are also within the invention.

In an aspect, the present invention realised a novel, isolated progenitor or stem cell (a vertebrate, preferably a mammal, even more preferably a human cell), originated from adult liver, characterised in that it co-expresses (i.e., is positive for) at least one mesenchymal marker, esp. one, more than one, e.g., 2, 3, or 4, or all of the markers CD90, CD44, CD73, vimentin and α-smooth muscle actin (ASMA), with the hepatocyte marker albumin (ALB) and possibly with one or more other hepatic or hepatocyte markers, preferably one, more than one, or all CD29, alpha-fetoprotein (AFP), alpha-1 antitrypsin and/or MRP2 transporter. The said adult liver progenitor or stem cell may further express one, more than one, or all of the following molecules indicative of hepatocyte-like properties or function: G6P, CYP1B1, CYP3A4, HNF-4, TDO, TAT, GS, GGT, CK8, EAAT2. The said adult liver progenitor or stem cell may further be characterised by one, more than one, or all of the following: negative for at least the hematopoietic markers CD45 and CD34 and possibly also for one or more other hematopoietic markers, such as, e.g., CD105, HLA-DR, negative for the cholangiocyte epithelial marker cytokeratin-19 (CK-19) and possibly for more epithelial markers; negative for at least the undifferentiated stem cell markers CD117 and Oct-4 and possibly also for one or more than one embryonic stem cell markers; low level expression of AFP. Preferably, the said adult liver progenitor or stem cell may have mesenchymal-like morphology, in particular involving one, more than one or all of growth in monolayers, flattened form, broad cytoplasm and/or ovoid nuclei with one or two nucleoli.

In an embodiment, in particular the present invention provides an isolated stem cell originated from adult liver, which is CD90, CD29 and CD44 positive which is albumin-positive, vimentin-positive and alpha smooth muscle actin-positive. In an embodiment, the isolated stem cells are also CK-19 negative, CD45 negative, CD 34 negative and CD117 negative. The present invention also provides a cell population comprising progenitor mesenchymal stem cells having at least three of the following characteristics: antibody-detectable expression of albumin; antibody-detectable expression of vimentin; antibody-detectable expression of alpha smooth muscle actin; absence of CK-19; absence of CD45, absence of CD45 marker, absence of CD34 marker, absence of CD117 marker, evidence of CD90 marker; evidence of CD29 marker; or evidence of CD44 marker. Preferably the cells have all the above listed characteristics. In a preferred embodiment, the stem cells are human liver stem cells.

In an embodiment, the isolated stem cell originated from adult liver is CD90, CD73, CD29 and CD44 positive and is albumin-positive, vimentin-positive and alpha smooth muscle actin-positive.

The invention also provides a method for obtaining an isolated progenitor or stem cell or a cell population comprising the said progenitor or stem cell, the method comprising: (a) disassociating adult liver or a part thereof to form a population of primary cells from the said adult liver or part thereof, (b) plating the primary cell population onto a substrate which allows adherence of cells thereto, and (c) culturing cells from the primary cell population, which have adhered to the said substrate, for at least 7 days, preferably at least 10, at least 13, or at least 15 days.

The present invention also provides a method for obtaining the isolated liver stem cell or the population thereof according to the invention comprising the steps of culturing cells from adult liver, isolating hepatocytes therefrom, plating the hepatocytes and culturing said hepatocytes for at least 7 days, preferably at least 10, at least 13, at least 15 days.

In a yet further aspect, the invention provides an isolated adult liver progenitor or stem cell, cell line thereof and/or a cell population comprising such, obtainable by or directly obtained using the methods of the invention.

In a further aspect, the present inventors have established a particular cell population (cell line) of adult human liver progenitor or stem cells according to the invention and deposited the said isolated cell line on Feb. 20, 2006 under the Budapest Treaty with the Belgian Coordinated Collections of Microorganisms (BCCM/LMBP) under accession number LMBP 6452CB (given by the International Depositary Authority; identification reference given by the depositor: ADHLSC). Accordingly, the present invention relates to an isolated cell, cell line and cell population deposited with BCCM under accession number LMBP 6452CB (herein, the "LMBP 6452CB" cell line), sub-lines thereof including clonal sub-lines, and to progeny thereof, including differentiated progeny thereof, esp. hepatocytes or hepatocytes-like cells prepared therefrom, and to genetically or otherwise modified derivatives thereof.

The present invention also provides a composition comprising the isolated liver progenitor or stem cell or the population thereof according to the invention. Preferably, the liver cells are human liver cells, or mammalian liver cells.

The progenitor or stem cells according to the invention (specifically mentioning, albeit of course not limited to the LMBP 6452CB line) entails several considerable advantages. For example, unlike cells of embryonic origin, the present progenitor or stem cells are of adult origin and may display lower risk of uncontrolled (tumour) growth or malignant transformation when used in therapy.

Furthermore, the inventors realised that the progenitor or stem cells according to the invention substantially do not display ability to differentiate into mesodermal cell types (e.g., osteocytes or chondrocytes, connective tissue cells), which decreases ectopic formation of such tissues when the cells are administered and implanted in liver tissue.

The present inventors also realised that the progenitor or stem cells of the invention may have particular preference for differentiation to hepatocytes or hepatocyte-like cells, which makes them particularly suitable for reconstitution of hepatocyte functions in a liver.

The present progenitor or stem cells are clearly different from previously described liver-derived stem cells, such as oval cells, e.g., in their morphological characteristics and marker expression.

The adult liver progenitor or stem cells according to the invention are particularly useful in medicine, hepatology, inborn errors of liver metabolism, transplantation, infectious diseases, liver failure. The liver progenitor or stem cells according to the invention are particularly useful for (human) liver cell transplantation, the preparation of animal models of human liver cell transplantation, bio-artificial livers, in vitro liver cell lines and animal models of acquired human liver diseases, liver metabolism screening tests (pharmacokinetics, cytotoxicity, genotoxicity) and liver cell directed gene therapy. The liver progenitor or stem cell according to the invention can be further differentiated into hepatocytes.

The present invention also provides a pharmaceutical composition comprising a liver progenitor or stem cell, cell line thereof or cell population thereof, or progeny thereof including differentiated progeny, esp. hepatocytes or hepatocyte-like cells, optionally genetically modified, according to the invention and a pharmaceutically acceptable carrier. Preferably, the liver cells are human liver cells, or mammalian liver cells.

The present invention also provides a method of treating liver disease comprising administering an effective amount of a liver progenitor or stem cell, a cell line thereof or cell population thereof, or progeny thereof including differentiated progeny, esp. hepatocytes or hepatocyte-like cells, optionally genetically modified, according to the invention. In an embodiment, the liver disease includes but is not limited to phenylketonuria and other aminoacidopathies, haemophilia and other clotting factor deficiencies, familial hypercholesterolemia and other lipid metabolism disorders, urea cycle disorders, glycogenosis, galactosemia, fructosemia, tyrosinemia, protein and carbohydrate metabolism deficiencies, organic aciduria, mitochondrial diseases, peroxysomal and lysosomal disorders, protein synthesis abnormalities, defects of liver cell transporters, defect of glycosylation, hepatitis, cirrhosis, inborn errors of metabolism, acute liver failure, acute liver infections, acute chemical toxicity, chronic liver failure, cholangitis, biliary cirrhosis, Alagille syndrome, alpha-1-antitrypsin deficiency, autoimmune hepatitis, biliary atresia, cancer of the liver, cystic disease of the liver, fatty liver, galactosemia, gallstones, Gilbert's syndrome, hemochromatosis, hepatitis A, hepatitis B, hepatitis C, and other hepatitis viral infections, porphyria, primary sclerosing cholangitis, Reye's syndrome, sarcoidosis, tyrosinemia, type 1 glycogen storage disease, or Wilson's disease.

The present invention also provides a method for treating errors of gene expression comprising: (i) introducing into a liver progenitor or stem cell, cell line thereof or cell population thereof, or progeny thereof including differentiated progeny, esp. hepatocytes or hepatocyte-like cells, according to the invention a functional copy of a gene to provide a transformed population; and (ii) introducing into a patient's liver, which patient is in need of the functional copy of the gene, at least a portion of the transformed population. Alternatively, the transformed population can be introduced into a non-human mammal's liver in order to produce a new animal model of hepatic pathology.

The present invention also provides a composition for treating errors of gene expression comprising a transformed liver progenitor or stem cell, cell line thereof or cell population thereof, or progeny thereof including differentiated progeny, esp. hepatocytes or hepatocyte-like cells, optionally genetically modified, according to the invention into which a functional copy of a gene has been introduced.

The present invention also provides a pharmaceutical composition for treating errors of gene expression comprising a liver progenitor or stem cell, cell line thereof or cell population thereof, or progeny thereof including differentiated progeny, esp. hepatocytes or hepatocyte-like cells, according to the invention into which a functional copy of a gene has been introduced and a pharmaceutically acceptable carrier.

The present invention also provides a method for enhancing the regeneration of an injured or diseased liver comprising administering into the liver an effective amount of a liver progenitor or stem cell, cell lines thereof or cell population thereof, or progeny thereof including differentiated progeny, esp. hepatocytes or hepatocyte-like cells, optionally genetically modified, according to the invention.

The present invention also provides a liver assist device comprising a housing harbouring a liver progenitor or stem cell, cell line thereof or cell population thereof, or progeny thereof including differentiated progeny, esp. hepatocytes or hepatocyte-like cells, optionally genetically modified, according to the invention.

The present invention also provides a method of conducting in vitro toxicity testing comprising: exposing to a test agent a liver progenitor or stem cell, a cell line thereof or cell population thereof, or progeny thereof including differentiated progeny, esp. hepatocytes or hepatocyte-like cells, optionally genetically modified, according to the invention, and observing at least one effect, if any, of the test agent on the population of liver cells. Preferably, the at least one effect includes an effect on cell viability, cell function, or both.

The present invention also provides a method of conducting in vitro drug metabolism studies comprising: (i) exposing a liver progenitor or stem cell, cell line thereof or cell population thereof, or progeny thereof including differentiated progeny, esp. hepatocytes or hepatocyte-like cells, optionally genetically modified, according to the invention, to a test agent, and (ii) observing at least one change, if any, involving the test agent after a predetermined test period. Preferably, the at least one change includes a change in the structure, concentration, or both of the test agent.

The present invention also provides a method of conducting testing for efficacious agents for treating liver infections comprising (i) infecting with an infectious agent of interest a liver progenitor or stem cell, cell line thereof or cell population thereof, or progeny thereof including differentiated progeny, esp. hepatocytes or hepatocyte-like cells, optionally genetically modified, according to the invention to provide an infected population, (ii) exposing the infected population to a predetermined amount of test agent, and (iii) observing effects, if any, of the exposure on the infected population. In an embodiment, the infectious agent includes a microorganism. In another embodiment, the infectious agent includes one or more viruses, bacteria, fungi, or combinations thereof. In a particular embodiment, the observed effects include effects on viral replication of a viral infectious agent. Preferably, the viral infectious agent includes a hepatitis virus.

The present invention also provides a method of producing a protein of interest comprising (i) introducing into a liver progenitor or stem cell, cell line thereof or cell population thereof, or progeny thereof including differentiated progeny, esp. hepatocytes or hepatocyte-like cells, according to the invention a functional gene encoding a protein of interest, (ii) incubating the said cell population under conditions effective for transcription, translation, and optionally post-translational modification to take place, and (iii) harvesting the protein of interest. Preferably the liver cells are human liver cells. In an embodiment, the protein of interest comprises a vaccine antigen.

The present invention also provides a method of conducting in vitro or in vivo studies on liver development and hepatocyte differentiation comprising: exposing a liver progenitor or stem cell, a cell line thereof or cell population thereof, or progeny thereof including differentiated progeny, according to the invention, in vitro or in vivo to conditions that affect differentiation conditions and observing at least one effect on the population of the cells.

The present invention encompasses the cells, the preparation thereof, the characterization thereof, the culture method thereof and the production thereof.

The present invention also encompasses the preservation of these cells by cryopreservation and the culture of the cells.

The present invention also encompasses the technique of transplantation of the cells in animals and humans.

The present invention also encompasses the use of the liver stem cell according to the invention for the preparation of a medicament for the treatment of the above mentioned diseases. The present invention also encompasses the use of the liver stem cell according to the invention in a kit or kit in part.

BRIEF DESCRIPTIONS OF THE FIGURES

FIG. 1 shows the morphological appearance of human adult liver derived progenitor or stem cells of the invention (ADHLSC), as prepared in example 1, after 1-month culture, using light microscopy (phase contrast). A, at lower confluence; B, at higher confluence. Magnification 100×

FIG. 2 A: presence of immuno-fluorescence staining of human adult liver derived progenitor or stem cells of the invention (ADHLSC), as prepared in example 1, after 1-month culture, for alpha-smooth muscle actin (A1), vimentin (A2) and albumin (A3, polyclonal, A4, monoclonal), B: RT-PCR gene expression profiles in the said (ADHLSC, lanes 1) cell line, compared to human hepatocytes (hHep, lanes 2), human stellate cells (hSC, lanes 3) and human hepatoblastoma (HepG2, lanes 4).

FIG. 3 shows differentiation of human adult liver derived progenitor or stem cells of the invention (ADHLSC) into hepatocytes-like lineage in vitro. Cells were differentiated as in example 1, photographs were taken on day 2 (J2), day 14 (J14) and day 30 (J30) of the process.

DETAILED DESCRIPTION

Figure 1:
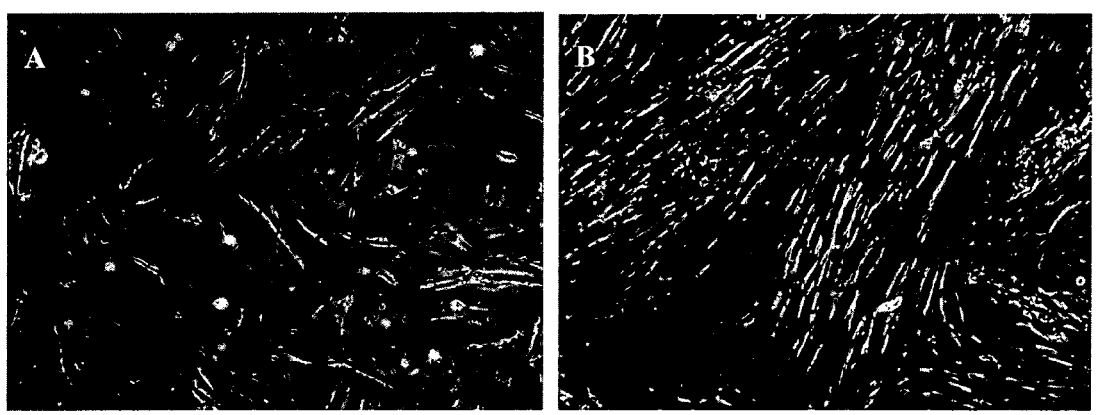

As used herein, the singular forms "a", "an", and "the" include both singular and plural referents unless the context clearly dictates otherwise. By way of example, "a cell" refers to one or more than one cell.

The terms "comprising", "comprises" and "comprised of" as used herein are synonymous with "including", "includes" or "containing", "contains", and are inclusive or open-ended and do not exclude additional, non-recited members, elements or method steps.

All references cited in the present specification are hereby incorporated by reference in their entirety. In particular, the teachings of all references herein specifically referred to are incorporated by reference.

Obtaining Cells of the Invention

In an aspect, the present invention provides a method for obtaining an isolated progenitor or stem cell or a cell population comprising the said progenitor or stem cell, the method comprising: (a) disassociating adult liver or a part thereof to form a population of primary cells from the said adult liver or part thereof, (b) plating the primary cell population onto a substrate which allows adherence of cells thereto, and (c) culturing cells from the primary cell population, which have adhered to the said substrate, for at least 7 days, preferably at least 10, at least 13, or at least 15 days.

As used herein, the term "isolated cell" refers generally to a cell that is not associated with one or more cells or one or more cellular components with which the cell is associated in vivo. For example, an isolated cell may have been removed from its native environment, or may result from propagation, e.g., ex vivo propagation, of a cell that has been removed from its native environment.

The term "in vitro" as used herein denotes outside, or external to, animal or human body. The term "in vitro" as used herein should be understood to include "ex vivd". The term "ex vivo" typically refers to tissues or cells removed from an animal or human body and maintained or propagated outside the body, e.g., in a culture vessel.

The term "cell population" refers generally to a grouping of cells. Unless indicated otherwise, the term refers to a cell grouping consisting of or comprising isolated cells as defined herein.

A cell population may consist of cells having a common phenotype or may comprise at least a fraction of cells having a common phenotype. Cells are said to have a common phenotype when they are substantially similar or identical in one or more demonstrable characteristics, including but not limited to morphological appearance, the presence, absence or level of expression of particular cellular components or products, e.g., RNA, proteins or other substances, activity of certain biochemical pathways, proliferation capacity and/or kinetics, differentiation potential and/or response to differentiation signals or behaviour during in vitro cultivation (e.g., adherence, non-adherence, monolayer growth, proliferation kinetics, or the like). Such demonstrable characteristics may therefore define a cell population or a fraction thereof.

When a cell population is said herein to be "heterogeneous", this generally denotes a cell population comprising two or more cells or fractions of cells not having a common phenotype, e.g., a cell population comprising cells of two or more different cell types. By means of example and not limitation, a heterogeneous cell population can be isolated from liver, and may comprise diverse liver cell types, including but not limited to hepatocytes (e.g., large and small hepatocytes), cholangiocytes, Kupffer cells, hepatic stellate cells (Ito cells) and liver endothelial cells.

When a cell population is said herein to be "homogeneous", it consists of cells having a common phenotype. A cell population said herein to be "substantially homogeneous" comprises a substantial majority of cells having a common phenotype. A "substantially homogeneous" cell population may comprise at least 70%, e.g., at least 80%, preferably at least 90%, e.g., at least 95%, or even at least 99% of cells having a common phenotype, such as the phenotype specifically referred to (e.g., the phenotype of progenitor cell or stem cell). As used herein, the term "substantially homogeneous" as used herein may thus also encompass a homogeneous population.

The term "cell population comprising a progenitor or stem cell" refers to a cell population as defined herein comprising at least one progenitor or stem cell and typically a fraction of progenitor cells or stem cells, as defined herein. Usually, the progenitor or stem cells of the said fraction may have a common phenotype.

The term "progenitor cell" refers generally to an unspecialised or relatively less specialised and proliferation-competent cell, which or the progeny of which can give rise to at least one relatively more specialised cell type. By means of example and not limitation, a progenitor cell may give rise to descendants that can differentiate along one or more lineages to produce increasingly relatively more specialised cells, wherein such descendants and/or increasingly relatively more specialised cells may themselves be progenitor cells, or even to produce terminally differentiated cells, i.e., fully specialised cells, which may be post-mitotic. The term also encompasses stem cells are defined herein.

A progenitor cell is said to "give rise" to another, relatively more specialised cell when, by means of example and not limitation, the progenitor cell differentiates to become the other cell without first undergoing cell division, or the other cell is produced after one or more rounds of cell division and/or differentiation of the progenitor cell or progeny thereof.

The term "stem cell" refers to a progenitor cell capable of self-renewal, i.e., can proliferate without differentiation, whereby the progeny of a stem cell or at least part thereof substantially retains the unspecialised or relatively less specialised phenotype, the differentiation potential, and the proliferation competence of the mother stem cell. The term encompasses stem cells capable of substantially unlimited self-renewal, i.e., wherein the capacity of the progeny or part thereof for further proliferation is not substantially reduced compared to the mother cell, as well as stem cells which display limited self-renewal, i.e., wherein the capacity of the progeny or part thereof for further proliferation is demonstrably reduced compared to the mother cell.

A skilled person knows that the above properties generally refer to the in vivo behaviour of progenitor and stem cells, and may under appropriate conditions be completely or at least in part replicated in vitro and/or ex vivo.

Based on the ability to give rise to diverse cell types, a progenitor or stem cell may be usually described as totipotent, pluripotent, multipotent or unipotent. A single "totipotent" cell is defined as being capable of growing, i.e. developing, into an entire organism. A "pluripotent" cell is not able of growing into an entire organism, but is capable of giving rise to cell types originating from all three germ layers, i.e., mesoderm, endoderm, and ectoderm, and may be capable of giving rise to all cell types of an organism. A "multipotent" cell is capable of giving rise to at least one cell type from each of two or more different organs or tissues of an organism, wherein the said cell types may originate from the same or from different germ layers, but is not capable of giving rise to all cell types of an organism. A "unipotent" cell is capable of differentiating to cells of only one cell lineage.

The terms "differentiation", "differentiating" or derivatives thereof as used herein denote the process by which an unspecialised or a relatively less specialised cell becomes relatively more specialised. In the context of cell ontogeny, the adjective "differentiated" is a relative term. Hence, a "differentiated cell" is a cell that has progressed further down a certain developmental pathway than the cell it is being compared with. A differentiated cell may, for example, be a terminally differentiated cell, i.e., a fully specialised cell that takes up specialised functions in various tissues and organs of an organism, and which may but need not be post-mitotic. In another example, a differentiated cell may also be a progenitor cell within a differentiation lineage, which can further proliferate and/or differentiate. Similarly, a cell is "relatively more specialised" if it has progressed further down a certain developmental pathway than the cell it is being compared with, wherein the latter is therefore considered "unspecialised" or "relatively less specialised". A relatively more specialised cell may differ from the unspecialised or relatively less specialised cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, etc., wherein such characteristics signify the progression of the relatively more specialised cell further along the said developmental pathway.

Non-limiting examples of differentiation may include, e.g., the change of a pluripotent stem cell into a given type of multipotent progenitor or stem cell, the change of a multipotent progenitor or stem cell into a given type of unipotent progenitor or stem cell, or the change of a unipotent progenitor or stem cell to more specialised cell types or to terminally specialised cells within a given cell lineage. Differentiation of an unspecialised or less specialised cell to a more specialised cell may proceed through appearance of cells with an intermediate degree of specialisation.

Disassociating Liver Tissue

As mentioned, the method of the invention comprises a step of disassociating adult liver or a part thereof to form a population of primary cells from the said adult liver or part thereof.

The term "liver" refers to liver organ. The term "part of liver" generally refers to any part of the liver organ, without any limitation as to the quantity of the said part or the region of the liver organ where it originates. Preferably, all cell types present in the liver organ may also be represented in the said part of liver. Quantity of the part of liver may at least in part follow from practical considerations, e.g., the need to obtain enough primary liver cells for reasonably practising the method of the invention. Such considerations will be apparent to a skilled person in view of the present teachings. Hence, by means of example and not limitation, a part of liver may represent (typically w/w) at least 0.1% of the liver, or at least 1%, or at least 10%, or at least 20%, or at least 30%, or at least 40%, or at least 50%, or at least 60%, or at least 70%, or at least 80%, or at least 90% or more of the liver organ. In other non-limiting examples, a part of liver may be at least 1 g, or at least 10 g, or at least 100 g, or at least 200 g, or at least 300 g, or at least 400 g, or at least 500 g, or at least 600 g, or at least 700 g, or at least 800 g, or at least 900 g, or at least 1000 g, or at least 1100 g, or at least 1200 g, or at least 1300 g, or at least 1400 g or more. For example, a part of liver may be a liver lobe, e.g., the right lobe or left lobe, or segment IV resected during split liver operation.

The term "adult liver" as used herein refers to liver which has attained substantial developmental maturity of tissue organisation and cell composition.

In particular, it is known to a skilled person that liver may undergo developmental changes during a time period immediately following birth, where after it attains a substantially mature organisation. For example, in human subjects, the liver at birth contains a considerable population of hematopoietic cells, which substantially disappear from the liver within about 1-2 weeks after birth. Moreover, the liver of human subjects at birth contains a population of hepatic progenitor cells, which are substantially replaced by mature hepatocytes and biliary cells within several months after birth.

Accordingly, in human subjects, "adult liver" refers to liver of subjects that are any time after birth, preferably full term, and may be, e.g., at least one month of age after birth, e.g., at least 2 months, at least 3 months, e.g., at least 4 months, at least 5 months, e.g., at least 6 months age after birth, such as, for example, 1 year or more, 5 years or more, at least 10 years or more, 15 years or more, 20 years or more, or 25 years or more of age after birth. Hence, an "adult liver", or mature liver, may be found in human subjects which would otherwise be described in the conventional terms of "infant", "child", "youth", "adolescent" or "adult".

A skilled person will appreciate that the liver may attain substantial developmental maturity in different time postnatal intervals in different animal species, and can properly construe the term "adult liver" with reference to each species.

The liver or part thereof is obtained from a "subject", "donor subject" or "donor", interchangeably referring to a vertebrate animal, preferably a mammal, more preferably a human.

The term "mammal" includes any animal classified as such, including, but not limited to, humans, domestic and farm animals, zoo animals, sport animals, pet animals, companion animals and experimental animals, such as, for example, mice, rats, rabbits, dogs, cats, cows, horses, pigs and primates, e.g., monkeys and apes.

In a particularly preferred embodiment, the adult liver or part thereof is from a human subject. As detailed elsewhere in the specification, progenitor or stem cells or cell lines, or progeny thereof, derived according to the invention from livers of human subjects, can be advantageously used, e.g., in research and in therapy of patients, esp. human patients, suffering from liver disease.

In another embodiment, the adult liver or part thereof may be from a non-human animal subject, preferably a non-human mammal subject. Progenitor or stem cells or cell lines, or progeny thereof, derived according to the invention from livers of non-human animal or non-human mammal subjects can be advantageously used, e.g., in research and in the therapy of liver disease in members of the same, related or other non-human animal or non-human mammal species, or even in the therapy of human patients suffering from liver disease (e.g., xenotransplantation, bio-artificial liver devices comprising non-human animal or non-human mammal cells). By means of example and not limitation, particularly suitable non-human mammal cells for use in human therapy may originate from pigs.

A donor subject may be living or dead, as determined by art-accepted criteria, such as, for example, the "heart-lung" criteria (usually involving an irreversible cessation of circulatory and respiratory functions) or the "brain death" criteria (usually involving an irreversible cessation of all functions of the entire brain, including the brainstem). Harvesting may involve procedures known in the art, such as, for example, biopsy, resection or excision.

A skilled person will appreciate that at least some aspects of harvesting liver or part thereof from donor subjects may be subject to respective legal and ethical norms. By means of example and not limitation, harvesting of liver tissue from a living human donor may need to be compatible with sustenance of further life of the donor. Accordingly, only a part of liver may typically be removed from a living human donor, e.g., using biopsy or resection, such that an adequate level of physiological liver functions is maintained in the donor. On the other hand, harvesting of liver or part thereof from a non-human animal may, but need not be compatible with further survival of the non-human animal. For example, the non-human animal may be humanely culled after harvesting of the tissue. These and analogous considerations will be apparent to a skilled person and reflect legal and ethical standards and are substantially not related to the essence of the invention.

In an embodiment, liver or part thereof may be obtained from a donor, esp. human donor, who has sustained circulation, e.g., a beating heart, and sustained respiratory functions, e.g., breathing lungs or artificial ventilation. Subject to ethical and legal norms, the donor may need to be or need not be brain dead (e.g., removal of entire liver or portion thereof, which would not be compatible with further survival of a human donor, may be allowed in brain dead human beings). Harvesting of liver or part thereof from such donors is advantageous, since the tissue does not suffer substantial anoxia (lack of oxygenation), which usually results from ischemia (cessation of circulation).

In another embodiment, and as surprisingly realised by the present inventors, liver or part thereof may be obtained from a donor, esp. human donor, who at the time of harvesting the tissue has ceased circulation, e.g., has a non-beating heart, and/or has ceased respiratory functions, e.g., has non-breathing lungs and no artificial ventilation. While liver or part thereof from these donors may have suffered at least some degree of anoxia, the present inventors realised that viable progenitor or stem cells according to the present invention can also be obtained from such tissues. Liver or part thereof may be harvested within about 24 h after the donor's circulation (e.g., heart-beat) ceased, e.g., within about 20 h, e.g., within about 16 h, more preferably within about 12 h, e.g., within about 8 h, even more preferably within about 6 h, e.g., within about 5 h, within about 4 h or within about 3 h, yet more preferably within about 2 h, and most preferably within about 1 h, such as, within about 45, 30, or 15 minutes after the donor's circulation (e.g., heart-beat) ceased.

The tissues harvested as above may be cooled to about room temperature, or to a temperature lower than room temperature, but usually freezing of the tissue or parts thereof is avoided, esp. where such freezing would result in nucleation or ice crystal growth. For example, the tissue may be kept at any temperature between about 1° C. and room temperature, between about 2° C. and room temperature, between about 3° C. and room temperature or between about 4° C. and room temperature, and may be advantageously be kept at about 4° C. The tissue may also be kept "on ice" as known in the art. The tissue may be cooled for all or part of the ischemic time, i.e., the time after cessation of circulation in the donor. That is, the tissue can be subjected to warm ischemia, cold ischemia, or a combination of warm and cold ischemia. The harvested tissue may be so kept for, e.g., up to 48 h before processing, preferably for less than 24 h, e.g., less than 16 h, more preferably for less than 12 h, e.g., less than 10 h, less than 6 h, less than 3 h, less than 2 h or less than 1 h.

The harvested tissue may advantageously be but need not be kept in, e.g., completely or at least partly submerged in, a suitable medium and/or may be but need not be perfused with the suitable medium, before further processing of the tissue. A skilled person is able to select a suitable medium which can support the survival of the cells of the tissue during the period before processing.

The method of the invention comprises disassociating adult liver tissue as described above to form a population of primary cells.

The term "disassociating" as used herein generally refers to partly or completely disrupting the cellular organisation of a tissue or organ, i.e., partly or completely disrupting the association between cells and cellular components of a tissue or organ. As can be understood by a skilled person, the aim of disassociating a tissue or organ is to obtain a suspension of cells (a cell population) from the said tissue or organ. The suspension may comprise solitary or single cells, as well as cells physically attached to form clusters or clumps of two or more cells. Disassociating preferably does not cause or causes as small as possible reduction in cell viability.

A suitable method for disassociating liver or part thereof to obtain a population (suspension) of primary cells therefrom may be any method well known in the art, including but not limited to, enzymatic digestion, mechanical separation, filtration, centrifugation and combinations thereof. In an embodiment, the method for disassociating liver or part thereof may comprise enzymatic digestion of the liver tissue to release liver cells. In an embodiment, the method for disassociating liver or part thereof may comprise mechanical disruption or separation of the liver tissue to release liver cells. In an embodiment, the method for disassociating liver or part thereof may comprise a combination of enzymatic digestion and mechanical disruption or separation of the liver tissue to release liver cells.

Methods for disassociating liver or part thereof as above are documented in the art. For example, isolation of liver cells from liver tissue has been well known since the mid-1960s (Howard et al. 1967. J Cell Biol 35: 675-84). Rat hepatocytes were isolated using a combined mechanical and enzymatic digestion technique, subsequently modified by Berry and Friend (J Cell Biol 43: 506-20, 1969). This technique was further developed by Seglen to become the widely used two-step collagenase perfusion technique (Methods Cell Biol 13: 29-83, 1976).

Accordingly in an embodiment, the method for disassociating liver or part thereof to obtain a population (suspension) of primary cells therefrom is or comprises two-step collagenase perfusion technique. A skilled person is aware that since the above publication of the said technique, various modifications thereof have been described and/or are conceivable, and are included in the invention.

By means of illustration and not limitation, brief description of a common two-step collagenase technique ensues. For whole livers, cannulae can be placed in the existing major blood vessels of the liver, and secured in place by sutures. For parts or segments of liver, cannulae can be placed in patent blood vessel openings on the cut surface, and secured by sutures. In this case, small blood vessel openings usually need to be sealed to prevent leakage of perfusion solutions from the cut surface. The liver tissue is perfused with a divalent cation-free buffer solution preheated at 37° C. containing a cation-chelating agent, such as, e.g., ethylenediamine tetraacetic acid (EDTA) or ethyleneglycol tetraacetic acid (EGTA). Buffer solutions can comprise salt solutions, such as, e.g., N-2-hydroxyethylpiperazine-N'-ethanesulfonic acid (HEPES), Williams E medium, Hank's balanced salt solution, or Earl's balanced salt solution, and can also include salts such as NaCl and KCl, among others. This leads to disruption of the desmosomal structures that hold cells together. The tissue is then perfused with the buffer solution containing divalent cation(s), such as $Ca^{2+}$ and $Mg^{2+}$, and matrix-degrading enzymes that act to digest the tissue. The primary liver cells, esp. hepatocytes, are usually released by gentle mechanical disruption, e.g., raking with a comb, shaking, pressing through filters, e.g., stainless steel filters, cheesecloth or nylon fabric, to mechanically complete the cell dissociation process. Such filters may have sieve sizes that allow passage of hepatocytes there through, by means of example and not limitation, about 0.1 mm or more, about 0.25 mm or more, about 0.50 mm or more, about 1 mm or more, or about 2 mm, 3 mm, 4 mm or 5 mm. A succession of filters with progressively smaller sieve sizes may be used to gradually disassociate the tissue and release cells. The dissociated cells are rinsed with a buffer containing protease inhibitor, serum and/or plasma to inactivate the collagenase and other enzymes used in the perfusion process, separated by low speed centrifugation, e.g., at between 10×g and 500×g (advantageously, substantially all live cells can be pelleted, while dead cells and cell debris are substantially eliminated), and the pellets obtained are washed with ice-cold buffer solution to purify the cell suspension.

The number and quality of the isolated liver cells can vary depending, e.g., on the quality of the tissue used, the compositions of perfusion buffer solutions, and the type and concentration of enzyme. Frequently used enzymes include, but are not limited to, collagenase, pronase, trypsin, dispase, hyaluronidase, thermolysin and pancreatin, and combinations thereof. Collagenase is most commonly used, often prepared from bacteria (e.g. from *Clostridium histolyticum*), and may often consist of a poorly purified blend of enzymes, which may have inconsistent enzymatic action. Some of the enzymes exhibit protease activity, which may cause unwanted reactions affecting the quality and quantity of viable/healthy cells. It is understood by those of skill in the art to use enzymes of sufficient purity and quality to obtain viable liver cell populations.

Other methods of harvesting primary liver cells may exclude enzymatic digestion techniques. Mechanical disruption has been widely used, although the yields of liver cells produced by this approach tend to be less than by collagenase digestion, as well as being less consistent. However, recent methods involving sucrose-EDTA perfusion in combination with controlled vibration in a cooled environment have been developed with reasonable success (Kravchenko et al. 2002. Cell Biol Int 26: 1003-1006). The liver perfusion is performed in situ using a solution of sucrose containing EDTA (pH 7.4). After perfusion, the liver is removed from the body, placed into a dish, and divided finely in a small volume of ice-cold medium. The cells of the liver fragments are liberated by means of controlled mechanical vibrational disaggregation (MVD), using a homogenizer motor. The resultant slurry produced by this method can then be filtered through coarse mesh to give an initial suspension of liver cells. The cells can be suspended in medium, and recovered by centrifugation. Accordingly, in an embodiment, the disassociation of liver or part thereof may be by mechanical disruption.

A skilled person is aware that two-step collagenase techniques may be particularly suited to release at least hepatocytes from liver tissue. Cell suspensions obtained using the said technique may comprise a considerable proportion of hepatocytes, and may also contain other liver cell types. As mentioned, the present inventors have realised that such cell suspensions are a particularly suitable starting material for obtaining the progenitor or stem cell of the invention.

In an embodiment, the method of disassociating liver or part thereof may form a cell suspension (as could be easily optimised by a skilled person) comprising at least 10%, e.g., at least 20%; at least 30%, e.g., at least 40%; at least 50%, e.g., at least 60%; at least 70%, e.g., at least 80%; or at least 90%, or up to about 100% of individual cells, i.e., single cells.

As mentioned, disassociating liver tissue thus provides a population of primary cells from the said adult liver or part thereof.

As used herein, the term "primary cell" includes cells present in a suspension of cells obtained from a tissue or organ of a subject, e.g., by disassociating thereof (i.e., a cell population prior to its being plated), cells present in an explanted tissue, both of the previous kinds of cells when first time plated, and cells of the cell suspensions derived from these first time plated cells. The term "secondary cell" refers to cells at all subsequent steps in cultivation. Hence, when primary cells plated for the first time are passaged, e.g., lifted from a substrate surface and re-plated, they are then referred to herein as secondary cells, as are all cells in subsequent passages.

The population of primary cells as defined and obtained herein by disassociating liver or part thereof may typically be heterogeneous, i.e., it may comprise cells belonging to more than one cell type that are comprised in liver. Exemplary liver-constituting cell types include but are not limited to hepatocytes, cholangiocytes (bile duct cells), Kupffer cells, hepatic stellate cells (Ito cells), oval cells and liver endothelial cells. The above terms have art-established meanings and are construed broadly herein as encompassing any cell type classified as such. Liver-constituting cell types further encompass both parenchymal and non-parenchymal liver cells.

By means of further illustration but not limitation, "hepatocyte" encompasses epithelial, parenchymal liver cells, including but not limited to hepatocytes of different sizes (e.g., "small", "medium-size" and "large" hepatocytes), ploidy (e.g., diploid, tetraploid, octaploid) or other characteristics. For example, some authors propose that "large" hepatocytes, as defined therein, are the parenchymal cells responsible for physiological functions of the liver, while "small" hepatocytes provide a reservoir progenitor cells committed to development towards hepatocytes (see, e.g., Mitaka et al. Biochem Biophys Res Commun 214: 310-7, 1995). Further by means of illustration and not limitation, "cholangiocytes" encompass epithelial cells of the bile ducts. Also by means of illustration and not limitation, "oval cell" encompass cells of distinctive morphology (e.g., nucleus shape) and cell marker expression, as known in the art, which are proposed to be progenitor cells capable, under certain conditions, of giving rise to hepatocytes and bile duct cells (Lowes et al. KN. 2003. J Gastroenterol Hepatol 18: 4-12; Yi et al 1999. J of Hepatology 31: 497-507).

Hence, in an embodiment, a heterogeneous population of primary liver cells may comprise cells of at least two, e.g., at least three or at least four or more liver-constituting cell types, e.g., cells belonging to all or substantially all liver-constituting cell types, including but not limited to the above listed liver cell types. A skilled person will appreciate that the heterogeneous population may comprise liver cell types which have been previously described as such, whether in vivo or in vitro, as well as liver cell types which have not been previously described, classified, isolated and/or characterised in the art.

A skilled person will also appreciate that the heterogeneous cell population may but need not comprise various liver cell types in the same or substantially the same relative proportions as present in the liver or part thereof having been disassociated. For example, a skilled person knows that particular manners of disassociating liver tissues may lead to more effective isolation of one or more cell types compared to one or more other cell types, whereby the obtained cell suspension may be inadvertently or purposefully enriched for the former one or more cell types. Moreover, some disassociating methods may differently affect the survival and/or viability of different liver cell types. Also, a skilled person is well aware of art methods for enriching a cell population obtained by disassociating liver or part thereof for one or more desired liver cell types. Such methods include but are not limited to differential centrifugation, buoyant density gradient centrifugation, filtration, cell elutriation, affinity purification, protease digestion, or the like.

In an embodiment, the heterogeneous population of primary liver cells may comprise cells belonging to all or substantially all liver-constituting cell types. The present inventors realised a method for obtaining a previously undisclosed type of progenitor or stem cell from liver. Nevertheless, the inventors wish not to be bound by any hypothesis as to the origin of the said novel progenitor or stem cell.

By means of example and not limitation, the said progenitor or stem cell, or an ancestor thereof, may have been present in liver, e.g., in parenchyma or non-parenchyma thereof. For example, such ancestor may have had a phenotype identical to, similar to or different from the isolated progenitor or stem cell (e.g., culturing according to the invention may have altered the phenotype of the ancestor). Alternatively, or in addition, the isolated progenitor or stem cell may have arisen due to alteration, e.g., differentiation or dedifferentiation, of one or more liver cell types, e.g., a liver cell type that has or has not been previously known. In view hereof, the method of the present invention may preferably start from a cell population representative of all or substantially all liver cell types.

The inventors have realised that the progenitor or stem cell of the invention can be advantageously obtained from a cell population formed by disassociating liver or part thereof, wherein the said cell population comprises hepatocytes. Hence, a suitable method for disassociating liver or part thereof according to the invention forms a cell population comprising hepatocytes. Without being bound to any theory, the inventors think that the progenitor or stem cell of the invention, or an ancestor thereof, is co-released from liver tissue by disassociating the liver in a manner which releases at least hepatocytes from the liver.

In an embodiment, the method of disassociating liver or part thereof may form a cell population comprising a proportion of hepatocytes which is at least about 10%, at least about 20%, at least 30%, at least 40%, preferably at least about 50%, e.g., at least 60%, more preferably at least about 70%, e.g., at least about 80%, even more preferably at least about 90% or more, such as at least about 95%, at least about 96%, at least about 97%, at least about 98%, or at least about 99%. The inventors realised that method of disassociating liver or part thereof which forms a cell population comprising a substantial proportion of hepatocytes, e.g., at least about 50% or more as above, provides suitable starting cell population for obtaining the progenitor or stem cell of the invention.

In a preferred embodiment, a cell population comprising the above proportions of hepatocytes may be obtained by disassociating liver or part thereof, without including steps for further enriching the cell population for hepatocytes and/or other cell types.

In another embodiment, a cell population comprising the above proportions of hepatocytes may be obtained by disassociating liver or part thereof and one or more further steps for enriching the cell population for hepatocytes and/or other cell types, esp. for hepatocytes. However, a skilled person will appreciate that while the progenitor or stem cell of the invention, or ancestor thereof, can be released from liver under disassociation conditions suitable for releasing hepatocytes therefrom, it may, but need not always, co-purify with hepatocytes, or one or more sub-groups of hepatocytes (e.g., "large" or "small" hepatocytes), or other cell types, in methods for enriching a cell population for hepatocytes, sub-groups thereof, or other cell types. It is within the ability of a skilled person to select methods for enriching hepatocytes or other cell types, esp. for hepatocytes, that retain the progenitor or stem cell of the invention, or ancestor thereof, in the resulting cell population.

Further, a skilled person will understand that the progenitor or stem cell of the invention, or an ancestor thereof, may have certain properties (e.g., physical properties or surface marker expression) which may allow its enrichment in the cell population obtained from liver, using a suitable separation technique. It may be within the reach of a skilled person to determine which fraction of a cell population separated on basis of one or more criteria comprises, or is enriched for, the progenitor or stem cell of the invention, or an ancestor thereof. This can be done, e.g., by cultivating cells from the various test fractions according to the method of the invention and ascertaining which fraction(s) yield the progenitor or stem cell of the invention.

An "enriched population" of cells refers to a population of cells in which one or more cell types are present in greater relative proportions than that which could be found in vivo or in the cell population subjected to enrichment.

Plating of Primary Cells from Liver Tissue

The method of the invention comprises culturing the primary cell population obtained by dissociating liver tissue as explained. To this aim, the primary population of liver cells is plated onto a substrate which allows adherence of cells thereto.

The term "plating" as used herein is synonymous to seeding or inoculating, and in general refers to introducing a cell population into an in vitro environment capable of promoting the survival and/or growth of the introduced cells. Typically, the said environment may be provided in a system which is suitably delimited from the surroundings, such that it can prevent an undesired exchange of matter between the said environment and the surroundings (thereby avoiding, e.g., contamination of the environment or escape of culture medium or cells therefrom), while it can allow for continuous or intermittent exchange of other, useful, matter components between the said environment and the surroundings (e.g., an occasional exchange of a part or all of the culture medium, the continuous exchange of gases, or the harvesting of the cells after culturing, etc.). Usually, environments suitable for culturing of cell can be generated in culture vessels well-known in the art, such as, e.g., cell culture flasks, well plates and dishes of various formats.

In the present invention, cells (e.g., primary liver cells) are plated onto a substrate which allows for adherence of cells thereto, i.e., a surface which is not generally repulsive to cell adhesion or attachment. This may be carried out, e.g., by plating the cells in a culture system (e.g., a culture vessel) which displays one or more substrate surfaces compatible with cell adhesion. When the said one or more substrate surfaces contact the suspension of cells (e.g., suspension in a medium) introduced into the culture system, cell adhesion between the cells and the substrate surfaces may ensue. Accordingly, the term "plating onto a substrate which allows adherence of cells thereto" refers to introducing cells into a culture system which features at least one substrate surface that is generally compatible with adherence of cells thereto, such that the plated cells can contact the said substrate surface. General principles of maintaining adherent cell cultures are well-known in the art.

In general, a substrate which allows adherence of cells thereto may be any substantially hydrophilic substrate. As known in the art, culture vessels, e.g., culture flasks, well plates, dishes, or the like, may be usually made of a large variety of polymeric materials, including, but not limited to polyacrylates, polymethylacrylates, polycarbonates, polystyrenes, polysulphones, polyhydroxyacids, polyanhydrides, polyorthoesters, polyphosphazenes, polyphosphates, polyesters, nylons or mixtures thereof, etc. Generally, culture vessels made of such materials are surface treated after moulding in order to provide for hydrophilic substrate surfaces and thereby enhance the likelihood of effective cell attachment. Surface treatment may take the form of a surface coating, or may involve the use of directed energy at the surface with the intention of generating chemical groups on the polymer surface. These chemical groups will have a general affinity for water or otherwise exhibit sufficient polarity to permit stable adsorption to another polar group. These functional groups lead to hydrophilicity and or an increase in surface oxygen and are properties recognized to enhance cell growth on so modified substrate surfaces. Such chemical groups may include groups such as amines, amides, carbonyls, carboxylates, esters, hydroxyls, sulfhydryls and the like. Examples of directed energy include atmospheric corona discharge, radio frequency (RF) vacuum plasma treatment, and DC glow discharge or plasma treatment (e.g., U.S. Pat. No. 6,617,152). Current standard practices for growing adherent cells may involve the use of defined chemical media with addition of bovine, human or other animal serum. The added serum, besides providing nutrients and/or growth promoters, may also promote cell adhesion by coating the treated plastic surfaces with a layer of matrix to which cells can better adhere.

An alternative substrate surface compatible with cell adhesion may be glass, optionally surface treated to introduce functional groups, e.g., as listed above, to increase the hydrophilicity thereof.

Other adherent substrate surfaces may be generated via surface coating, e.g., coating of the polymeric or treated polymeric surfaces as above. In a non-limiting example, the coating may involve suitable poly-cations, such as, e.g., poly-ornithine or poly-lysine.

In another example, preferred coating, and accordingly the substrate, comprises one or more components of extracellular matrix, e.g., the ECM proteins fibrin, laminin, collagen, preferably collagen type 1, glycosaminoglycans, e.g., heparin or heparan sulphate, fibronectin, gelatine, vitronectin, elastin, tenascin, aggrecan, agrin, bone sialoprotein, cartilage matrix protein, fibrinogen, fibulin, mucins, entactin, osteopontin, plasminogen, restrictin, serglycin, To facilitate said adherence, in embodiments, the primary cell suspension may be contacted with the adherent surface for at least about 0.5 h, e.g., for at least about 1 h, preferably for at least about 2 h, e.g., for at least about 4 h, more preferably for at least about 8 h, e.g., for at least about 12 h, even more preferably for at least about 16 h, e.g., for at least about 20 h, and most preferably for at least about 24 h or more, e.g., for at least about 28, 32, 36, 40, 44 or 48 h.

In other preferred embodiments, the primary cell suspension may be contacted with the adherent surface for between about 2 h and about 48 h, e.g., for between about 12 h and about 48 h, preferably for between about 12 h and about 36 h, e.g., for between about 16 h and about 32 h, even more preferably for between about 20 h and about 28 h, and most preferably for about 24 h.

While the above times are preferred, shorter or longer may also provide for attachment of cells compatible with the present invention, and a skilled person can optimise such times.

After cells from the primary liver cell population are allowed to attach to adherent substrate as described above, non-adherent matter is removed from the culture system. Non-adherent matter may comprise, but is not limited to, cells that have not attached to the adherent substrate (such as, e.g., cells which are not prone to adherence, or cells which would not attach within the time allowed therefore), non-viable or dead cells, cell debris, etc. Non-adherent matter can be typically removed by discarding medium from the culture system, whereupon adherent cells remain attached to the substrate, and optionally washing, once or repeatedly, the adherent cells and the culture system with suitable medium or isotonic buffer (e.g., PBS). Hereby, cells from the primary liver cell population, which have adhered to the substrate surface, are selected for further culturing.

The environment in which the cells are plated and allowed to attach may comprise at least a medium, in the methods of the invention typically a liquid medium, which supports the survival and/or growth of the cells. The medium may be added to the system before, together with or after the introduction of the cells thereto. The medium may be fresh, i.e., not previously used for culturing of cells, or may comprise at least a portion which has been conditioned by prior culturing of cells therein, e.g., culturing of the cells which are being plated or antecedents thereof, or culturing of cells more distantly related to or unrelated to the cells being plated. SPARC/osteonectin, versican, thrombospondin 1, or cell adhesion molecules including cadherins, connexins, selectins, by themselves or in various combinations.

Preferred examples may include fibrin, laminin or collagen. Further preferred examples may involve compositions comprising ECM components, such as, e.g., Matrigel® Basement Membrane Matrix (BD Biosciences), which is solubilised basement membrane preparation extracted from EHS mouse sarcoma, a tumour rich in ECM proteins, with laminin as a major component, followed by collagen type 4, heparan sulphate proteoglycans, and entactin.

A particularly preferred embodiment includes coating consisting of or comprising collagen, esp. collagen type 1.

As appreciated by those skilled in the art, the cells may be counted in order to facilitate subsequent plating of the cells at a desired density. Where, as in the present invention, the cells after plating may primarily adhere to a substrate surface present in the culture system (e.g., in a culture vessel), the plating density may be expressed as number of cells plated per $mm^2$ or $cm^2$ of the said substrate surface. In the present invention, the plating density of the primary cells obtained from disassociating liver or part thereof may be between 1 cell/$mm^2$ and $1 \times 10^6$ cells/$mm^2$, e.g., between $1 \times 10^1$ and $1 \times 10^5$ cells/$mm^2$ or between $1 \times 10^2$ and $1 \times 10^5$ cells/$mm^2$, e.g., between $1 \times 10^3$ and $1 \times 10^5$ cells/$mm^2$, between $5 \times 10^3$ and $5 \times 10^4$ cells/$mm^2$, between $1 \times 10^1$ and $1 \times 10^3$ cells/$mm^2$, between $1 \times 10^2$ and $1 \times 10^4$ cells/$mm^2$, e.g., about $1 \times 10^1$, $5 \times 10^1$, $1 \times 10^2$, $5 \times 10^2$, $1 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, or $1 \times 10^5$, cells/$mm^2$.

Typically, after plating of the primary liver cells, the cell suspension is left in contact with the adherent surface to allow for adherence of cells from the cell population to the said substrate. In contacting the primary liver cells with adherent substrate, the cells may be advantageously suspended in an environment comprising at least a medium, in the methods of the invention typically a liquid medium, which supports the survival and/or growth of the cells. The medium may be added to the system before, together with or after the introduction of the cells thereto. The medium may be fresh, i.e., not previously used for culturing of cells, or may comprise at least a portion which has been conditioned by prior culturing of cells therein, e.g., culturing of the cells which are being plated or antecedents thereof, or culturing of cells more distantly related to or unrelated to the cells being plated.

The medium may be a suitable culture medium as described elsewhere in this specification. Preferably, the composition of the medium may have the same features, may be the same or substantially the same as the composition of medium used in the ensuing steps of culturing the attached cells. Otherwise, the medium may be different. Advantageously, the medium can comprise serum or plasma, which may further facilitate cell adherence.

Culturing the Primary Cells from Liver Tissue

Cells from the primary cell population, which have adhered to the said substrate, preferably in the said environment, are subsequently cultured for at least 7 days, e.g., for at least 8 days or for at least 9 days, preferably for at least 10 days, e.g., at least 11 or at least 12 days, at least 13 days or at least 14 days, more preferably for at least 15 days, e.g., for at least 16 days or for at least 17 days, or even for at least 18 days, e.g., for at least 19 days or at least 20 days or more. The term "culturing" is common in the art and broadly refers to maintenance and/or growth of cells and/or progeny thereof.

In embodiments, the primary cells may be cultured for at least between about 10 days and about 40 days, preferably for at least between about 15 days and about 35 days, e.g., for at least between about 15 days and 20 days, such as for at least about 15, 16, 17, 18, 19 or 20 days. Preferably, the primary cells may be so cultured for no longer than 60 days, or no longer than 50 days, or no longer than 45 days.

As appreciated by those skilled in the art, prolonged culturing of cells in a culture system may necessitate regular exchange of the culture medium for a fresh medium. A skilled person is capable of assessing the need for exchanging the medium by inspecting the cell culture parameters, such as, e.g., the pH thereof, the cell density or cell appearance. Typically, the medium may be changed at regular intervals, e.g., every 1 to 10 days, preferably between 16 and 32 hours (e.g., about 24 hours) after plating and then preferably every 2 to 6 days, or more preferably every 2 to 4 days, e.g., about every 2, 3 or 4 days. The whole volume of the medium may be changed or, alternatively, only part of the medium may be changed, such that a portion of the medium conditioned by the previous culturing of the cells is retained. In an embodiment, substantially the whole volume of medium is exchanged for fresh medium. In another preferred embodiment, the medium is not exchanged during prolonged culturing of the cells.

The primary cell suspension and the further adherent cells are cultured in the presence of a liquid culture medium. Typically, the medium will comprise a basal medium formulation as known in the art. Many basal media formulations (available, e.g., from the American Type Culture Collection, ATCC; or from Invitrogen, Carlsbad, Calif.) can be used to culture the primary cells herein, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of the above basal media are generally known in the art and it is within the skill of one in the art to modify or modulate concentrations of media and/or media supplements as necessary for the cells cultured. In an embodiment, a preferred basal medium formulation may be Williams Medium E, which is a rich formulation reported to sustain in vitro culture of adult liver cells. Other embodiments may employ further basal media formulations, such as chosen from the ones above.

Such basal media formulations contain ingredients necessary for mammal cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g. glucose, pyruvate, e.g., sodium pyruvate, acetate, e.g., sodium acetate), etc. It will also be apparent that many media are available as low-glucose formulations with or without sodium pyruvate.

For use in culture, basal media can be supplied with one or more further components. For example, additional supplements can be used to supply the cells with the necessary trace elements and substances for optimal growth and expansion. Such supplements include insulin, transferrin, selenium salts, and combinations thereof. These components can be included in a salt solution such as, but not limited to, Hanks' Balanced Salt Solution (HBSS), Earle's Salt Solution. Further antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to D-aldosterone, diethylstilbestrol (DES), dexamethasone, estradiol, hydrocortisone, insulin, prolactin, progesterone, somatostatin/human growth hormone (HGH), thyrotropin, thyroxine, L-thyronine, epithelial growth factor (EGF) and hepatocyte growth factor (HGF). Liver cells can also benefit from culturing with tri-iodithyronine, α-tocopherol acetate, and glucagon.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture medium with mammalian plasma or sera. Plasma or sera often contain cellular factors and components that are necessary for viability and expansion. The use of suitable serum replacements is also contemplated.

The term "plasma" is as conventionally defined. Plasma is usually obtained from a sample of whole blood, which is provided or contacted with an anticoagulant, such as heparin, citrate (e.g., sodium citrate or acid citrate dextrose), oxalate or EDTA, upon or shortly after drawing the blood sample, to prevent clotting. Subsequently, cellular components of the blood sample are separated from the liquid component (plasma) by an appropriate technique, typically by centrifugation. The term "plasma" therefore refers to a composition which does not form part of a human or animal body.

The term "serum" is as conventionally defined. Serum can be usually obtained from a sample of whole blood by first allowing clotting to take place in the sample and subsequently separating the so formed clot and cellular components of the blood sample from the liquid component (serum) by an appropriate technique, typically by centrifugation. An inert catalyst, e.g., glass beads or powder, can facilitate clotting. Advantageously, serum can be prepared using serum-separating vessels (SST) known in the art, which contain the inert catalyst to facilitate clotting and further include a gel with density designed to become positioned between the liquid component and the clot and cellular components after centrifugation, thus simplifying separation. Alternatively, serum can be obtained from plasma by removing the anticoagulant and fibrin. The term "serum" hence refers to a composition which does not form part of a human or animal body.

The isolated plasma or serum can be used directly in the methods of the present invention. They can also be appropriately stored for a later use in the method of the present invention. Typically, plasma or serum can be stored for shorter time periods, e.g., up to about 1-2 weeks, at a temperature above the respective freezing points of plasma or serum, but below ambient temperature. Usually, this temperature will be about 15° C. or less, preferably about 10° C. or less, more preferably about 5° C. or less, e.g., about 5° C., 4° C., 3° C., 2° C. or about 1° C., most preferably about 5° C. or about 4° C. Alternatively, plasma or serum can be stored at below their respective freezing points, i.e., by freeze storage. As usual in the art, advantageous temperatures for freeze storage of plasma or serum can be about −70° C. or less, e.g., about −75° C. less or about −80° C. or less. Such temperatures may advantageously prevent any thawing of the stored plasma or serum, thereby preserving the quality thereof. Freeze storage can be used irrespective of the time period for which the plasma or serum need to be stored, but may be particularly suitable if longer storage is required, e.g., for longer than a few days or for longer than 1-2 weeks.

Prior to storage or use, the isolated plasma or serum can be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure.

Optionally, the plasma or serum may also be sterilised prior to storage or use. Usual means of sterilisation may involve, e.g., filtration through one or more filters with pore size smaller than 1 μm, preferably smaller than 0.5 μm, e.g., smaller than 0.45 μm, 0.40 μm, 0.35 μm, 0.30 μm or 0.25 μm, more preferably 0.2 μm or smaller, e.g., 0.15 μm or smaller, 0.10 μm or smaller.

Suitable sera or plasmas for use in the media of the present invention may include human serum or plasma, or serum or plasma from non-human animals, preferably non-human mammals, such as, e.g., non-human primates (e.g., lemurs, monkeys, apes), foetal or adult bovine, horse, porcine, lamb, goat, dog, rabbit, mouse or rat serum or plasma, etc. In another embodiment, the invention foresees the use of any combination of the above plasmas and/or sera.

Accordingly, in an embodiment, the serum or plasma may be obtained from an organism of the same species as is the species from which the primary liver cells are obtained. In a non-limiting example, human serum or plasma may be used for culturing primary human liver cells.

In another preferred embodiment, the medium comprises bovine serum or plasma, preferably foetal bovine (calf) serum or plasma, more preferably foetal bovine (calf) serum (FCS or FBS).

In another embodiment, the medium used to culture primary human liver cells comprises bovine serum or plasma, preferably foetal bovine (calf) serum or plasma, more preferably foetal bovine (calf) serum (FCS or FBS).

In embodiments, the medium comprises between about 0.5% and about 40% (v/v) of serum or plasma or serum replacement, preferably between about 5% and 20% (v/v), e.g., between about 5% and 15% (v/v), more preferably between about 8% (v/v) and about 12% (v/v), e.g., about 10% (v/v) of serum or plasma or serum replacement, esp. the preferred serum or plasma as defined above.

In a further preferred embodiment, the medium used to culture primary human liver cells comprises bovine serum or plasma, preferably foetal bovine (calf) serum or plasma, more preferably foetal bovine (calf) serum (FCS or FBS), in the amount of between about 0.5% and about 40% (v/v), preferably between about 5% and 20% (v/v), e.g., between about 5% and 15% (v/v), more preferably between about 8% (v/v) and about 12% (v/v), e.g., about 10%.

In yet other embodiments, a medium may comprise plasma or serum derived from more than one species. For example, the medium may comprise a mixture of serum or plasma derived from a species corresponding to the cultured primary liver cells, and from another species. For example, a medium for culturing human liver cells may comprise a mixture of human plasma or serum, preferably human serum, and bovine plasma or serum, preferably bovine serum. Further, the medium may preferably comprise at least one exogenously (i.e., in addition to the plasma or serum) added growth factor. A skilled person would appreciate that the ordinary components of basal media (before addition of serum or plasma), e.g., in particular, isotonic saline, buffers, inorganic salts, amino acids, carbon sources, vitamins, antioxidants, pH indicators and antibiotics, are not considered growth factors or differentiation factors in the art. On the other hand, serum or plasma is a complex composition possibly comprising one or more such growth factors or differentiation factors.

The term "growth factor" as used herein refers to a biologically active substance which influences proliferation, growth, differentiation, survival and/or migration of various cell types, and may effect developmental, morphological and functional changes in an organism, either alone or when modulated by other substances. A growth factor may typically act by binding, as a ligand, to a receptor (e.g., surface or intracellular receptor) present in cells responsive to the growth factor. A growth factor herein may be particularly a proteinaceous entity comprising one or more polypeptide chains.

By means of example and not limitation, the term "growth factor" encompasses the members of the fibroblast growth factor (FGF) family, bone morphogenic protein (BMP) family, platelet derived growth factor (PDGF) family, transforming growth factor beta (TGF-beta) family, nerve growth factor (NGF) family, the epidermal growth factor (EGF) family, the insulin related growth factor (IGF) family, the hepatocyte growth factor (HGF) family, hematopoietic growth factors (HeGFs), the platelet-derived endothelial cell growth factor (PD-ECGF), angiopoietin, vascular endothelial growth factor (VEGF) family, glucocorticoids, and the like.

In a preferred embodiment, the medium comprises a growth factor which is a member of the epidermal growth factor (EGF) family. In a further embodiment, the said member of the EGF family is any chosen from the group consisting of amphiregulin, betacellulin, EGF, epiregulin, HB-EGF (heparin-binding EGF-like growth factor), NRG1 (neuregulin-1) isoform GGF2, NRG1 isoform SMDF, NRG1-alpha, NRG1-beta, TGFalpha, Tomoregulin-1 and TMEFF2. In a particularly preferred embodiment, the medium comprises EGF.

In a further embodiment, the medium comprises a growth factor which is a member of the insulin related growth factor (IGF) family. In a further embodiment, the said member of the IGF family is any chosen from the group consisting of insulin, IGF1A (insulin-like growth factor 1A), IGF1B, IGF2, INSL3 (insulin-like 3), INSL5, INSL6 and relaxin. In a particularly preferred embodiment, the medium comprises insulin.

In a further embodiment, the medium comprises a growth factor which is a glucocorticoid. In a further embodiment, the said glucocorticoid is any chosen from the group consisting of dexamethasone, hydrocortisone, prednisolone, methylprednisolone, prednisone, triamcinolone, corticosterone, fluocinolone, cortisone, betamethasone. In a particularly preferred embodiment, the medium comprises dexamethasone.

In further preferred embodiments, the medium may comprise a combination of any two or more exogenously added growth factors or preferred growth factors as defined above. By means of example an not limitation, the medium may comprise EGF and insulin, or EGF and dexamethasone, or insulin and dexamethasone, or each EGF, insulin and dexamethasone; a medium comprising these exogenously added growth factors may preferably comprise serum or plasma as defined in the above embodiments.

A skilled person is in general knowledgeable of concentrations in which particular growth factors can induce an effect, esp. on in vitro cultured cells, and can use such concentrations for the above recited growth factors. By means of example and not limitation, EGF may be typically used at concentrations between about 0.1 ng/ml and 1 μg/ml and preferably between 1 ng/ml and 100 ng/ml, e.g., at about 25 ng/ml; insulin can be typically used at concentrations between about 0.1 μg/ml and 1 mg/ml and preferably between about 1 μg/ml and 100 µg/ml, e.g., at about 10 µg/ml; dexamethasone can be typically used at concentrations between about 0.1 nM and 1 µM, preferably between about 1 nM and 100 nM, e.g., at about 10 nM.

In a preferred embodiment, esp. where the method is used for human liver cells, the growth factor used in the present method may be a human growth factor. As used herein, the term "human growth factor" refers to a growth factor substantially the same as a naturally occurring human growth factor. For example, where the growth factor is a proteinaceous entity, the constituent peptide(s) or polypeptide(s) thereof may have primary amino acid sequence identical to a naturally occurring human growth factor. The use of human growth factors in the present method is preferred, as such growth factors are expected to elicit a desirable effect on cellular function.

As described, the present inventors have realised that by culturing primary liver cells for time durations as defined above, and preferably using media compositions as described above, a progenitor or stem cell of the invention emerges and proliferates, while differentiated liver cell types become less prevalent in the prolonged culturing of the primary liver cells. Without being limited to any hypothesis, the differentiated liver cell types may, for example, fail to proliferate, die and/or retro-differentiate during the prolonged culturing. As detailed in the experimental section, the progenitor or stem cell may be distinguished from other cell types present in the primary cell culture by, among others, its morphology, which according to the inventors' knowledge may be denoted as mesenchymal or mesenchymal-like morphology and may typically comprise a flattened form, broad cytoplasm and ovoid nuclei with one or two nucleoli.

The inventors also realised that the emergence, proliferation and enrichment of the primary culture for the said progenitor or stem cell may be further promoted by altering the culture medium such that this favours further elimination of one or more differentiated liver cell types, esp. of hepatocytes which may prevail in a culture of isolated primary liver cells. In such conditions, the progenitor or stem cell of the invention can advantageously proliferate and become a prevalent cell type in the primary liver cell culture. The differentiated liver cell types can be lost, e.g., because one or more differentiated cell types are physically decreased or eliminated during culture; alternatively, the differentiated phenotypes can be decreased because one or more cell types retro-differentiates during culture.

Any medium which favours the elimination of one or more differentiated liver cell types, esp. hepatocytes, while sustaining the proliferation of the progenitor or stem cell of the invention (as can be readily judged, for example, by visual inspection of the cell culture for the prevalence of the different cell types) can be used. By means of illustration, as exemplified by the inventors, one alteration may be the use of a basal medium comprising high glucose concentration, e.g., a concentration between 3000 mg/l and 6000 mg/l, preferably between 4000 mg/l and 5000 mg/l, and typically about 4500 mg/l. A further alteration may be the absence of exogenously added (i.e., in addition to those present in the serum or plasma) growth factors. By means of an example, at least exogenously added insulin, dexamethasone and/or EGF may be absent from the medium. Yet a further alteration may be the use of basal medium other than Williams Medium E (which may be particularly suited for long-term culture of primary liver cell types, esp. hepatocytes). By means of example and not limitation, basal media such as MEM, DMEM, alpha-MEM or EMEM may be advantageously used. It is to be understood that the medium may be altered in one, more than one or all of the above ways. It is further to be understood that the medium comprises serum or plasma or serum replacement as described above, including the above detailed preferred embodiments thereof.

In an embodiment, a medium favouring elimination of one or more differentiated liver cell types and promoting the progenitor or stem cell of the invention as described above may be added at the outset of culturing of the primary liver cells. In another embodiment, the medium may be so altered during the prolonged culturing of the primary liver cells. By means of example, the medium may be so altered starting at about 1 day, at about 2 days, 3 days, e.g., at about 4 or 5 days, or starting at about 6 days, such as, e.g., at about 7 or 8 days, or starting at about 9 days, such as e.g., at about 10 or 11 days, starting at about 12 days, e.g., at about 13 or 14 days, more preferably starting at about 15 days, e.g., at about 16, 17, 18, 19 or 20 days following plating of the primary liver cells. In an exemplary embodiment, the medium may be so altered at between 16 and 32 hours following plating, e.g., at about 24 hours. In embodiments, after the medium is so altered, it can be exchanged/refreshed, e.g., every 2 to 6 days, preferably every 2 to 4 days, e.g., every 3 or 4 days.

Hence, in an exemplary preferred embodiment, primary liver cells may be cultured following plating in a medium favouring survival of primary liver cell types, including differentiated liver cell types, such as hepatocytes, and at the above time the medium may be altered to a medium favouring elimination of one or more differentiated liver cell types, incl. hepatocytes, and promoting the progenitor or stem cell of the invention. For example, primary liver cells may first be cultured in a medium having one, more than one or all of the following features: comprising a rich basal medium, such as, e.g., Williams Medium E, comprising low glucose, e.g., between 500 mg/l and 2999 mg/l, and preferably between 1000 mg/l and 2000 mg/l, comprising at least one exogenously added growth factor and preferably one, more than one or all of insulin, dexamethasone and EGF. Thereafter, at the above times, the medium may be altered to include one, more than one or all of the following features: comprising basal medium other than Williams Medium E, e.g., basal media such as MEM, DMEM, alpha-MEM or EMEM, comprising high glucose, not comprising exogenously added growth factors or not comprising at least dexamethasone, insulin and/or EGF. It is to be understood that the above media would comprise serum or plasma or serum replacement as described above, including the above detailed preferred embodiments thereof.

As described, the above culturing of primary liver cells leads to emergence and proliferation of a progenitor or stem cell of the invention in the culture. The said culturing can be advantageously continued until the emerging progenitor or stem cell of the invention have proliferated sufficiently. For example, the said culturing can be continued until the cell population achieved a certain degree of confluence, e.g., at least 40%, preferably at least 50%, more preferably at least 60% and even more preferably at least 70%, e.g., at least 80% or at least 90% or more confluence. The term "confluence" as used herein refers to a density of cultured cells in which the cells contact one another covering substantially all of the surfaces available for growth (i.e., fully confluent).

Passaging of the Cells

Following the above culturing of the primary liver cells and emergence and proliferation of the progenitor or stem cells of the invention, the cell population so obtained may be passaged at least once.

The present inventors surprisingly realised that the progenitor or stem cells of the invention that emerged in the primary cell culture substantially retain their proliferation capacity after passaging, which thus allows to advantageously further enrich the cell population for these cells. For sake of simplicity, the passage performed at this stage of the method is herein referred to as "first passage" (or passage 1) within the method of the invention. The cells may be passaged at least one time and preferably two or more times. Each passage subsequent to passage 1 is referred to herein with a number increasing by 1, e.g., passage 2, 3, 4, 5, etc.

When passaged, the cultured cells are detached and dissociated from the culture substrate and from each other. Detachment and dissociation of the cells can be carried out as generally known in the art, e.g., by enzymatic treatment with proteolytic enzymes (e.g., chosen from trypsin, collagenase, e.g., type I, II, III or IV, dispase, pronase, papain, etc.), treatment with bivalent ion chelators (e.g., EDTA or EGTA) or mechanical treatment (e.g., repeated pipetting through a small bore pipette or pipette tip), or any combination of these treatments. Preferably, the detachment and dissociation of the cultured cells would yield a substantial proportion of the cells as single cells. For example, 40% or more of the cells can be recovered as single cells, e.g., at least 50%, preferably at least 60%, e.g., at least 70%, more preferably at least 80%, e.g., at least 90% or at least 95% of the cells may be recovered as single cells. Moreover, the remaining cells may be present in cell clumps or clusters the majority of which can contain a relatively small number of cells, e.g., on average, between more than 1 and 10 cells, e.g., less than 8 cells, preferably less than 6 cells, more preferably less than 4 cells, e.g., less than 3 or less than 2 cells.

Typically, a suitable method of cell detachment and dispersion should preserve viability of the cells. Preferably, a cell suspension obtained following detachment and dispersion may comprise at least 60% of viable cells, e.g., at least 70%, more preferably at least 80%, and most preferably at least 90% and up to 100% of viable cells. A skilled person will know in general to choose conditions which ensure a desired degree of cell detachment and dispersion, while preserving cell viability.

Next, the so detached and dissociated cells (typically as a cell suspension in an isotonic buffer or a medium) are re-plated onto a substrate which allows for adherence of cells thereto, and are subsequently cultured in a medium as described above sustaining the further proliferation the progenitor or stem cells of the invention. Typically, the cells may be re-plated at plating density of between $1 \times 10^1$ and $1 \times 10^6$ cells/cm$^2$, e.g., between $1 \times 10^2$ and $1 \times 10^6$ cells/cm$^2$, and preferably between $1 \times 10^3$ and $1 \times 10^5$ cells/cm$^2$, e.g., at about $1 \times 10^3$ cells/cm$^2$, at about $5 \times 10^3$ cells/cm$^2$, at about $1 \times 10^4$ cells/cm$^2$, at about $5 \times 10^4$ cells/cm$^2$, or at about $1 \times 10^5$ cells/cm2, and preferably at between about $1 \times 10^3$ and $1 \times 10^4$ cells/mm$^2$.

Alternatively, the cells may be re-plated at a splitting ratio of, e.g., between about ⅛ and ½, preferably between about ¼ and ½, and more preferably at about ½ or about ⅓. The splitting ratio denotes the fraction of the passaged cells which is seeded into an empty (typically a new) culture vessel of the same surface area as the vessel from which the cells were obtained.

The adherent substrate onto which the cells are re-plated is as described in detail elsewhere in this specification. The substrate may preferably be of the same kind as the substrate onto which the primary liver cells were plated, including preferred embodiments of such substrate described above, or may be different. Preferably, this substrate is also collagen, esp. collagen type I as described above.

The so passaged cells are further cultured, advantageously until the cells have become at least 50% confluent, e.g., at least 60%, preferably at least 70%, e.g., at least 80%, more preferably at least 90%, e.g., at least 95% or even fully confluent.

The present inventors have realised that while the cell population obtained at this stage of the method comprises a substantial fraction of the progenitor or stem cells of the invention, it can be advantageously passaged at least one more time (i.e., at least a second passage), essentially as described above for the first passage. This further increases the proportion of progenitor or stem cells of the invention in the cell population, as judged by morphology and/or marker analysis, and even a substantially homogeneous population of the progenitor or stem cells of the invention may be obtained.

Hence, according to the invention, following the plating and culture of primary liver cells leading to emergence and proliferation of the progenitor or stem cells in the said culture, the cultured cells are passaged at least once (i.e., first passage) and preferably at least two times (i.e., first and second passage), and optionally more times (i.e., first, second and each subsequent passage). For example, the cells may be passaged at least once, at least 2 times, at least 3 times, at least 4 times or at least 5 times following the plating of primary liver cells. In another embodiment, the cells may be passaged between 2 and 10 times, e.g., between 2 and 8 times, or between 2 and 5 times, following the plating of primary liver cells. The additional passages (e.g., cell detachment and dispersion, replating, substrate, etc.) and culturing (e.g., medium, medium changes, resulting confluence, etc.) may be performed at conditions substantially identical or analogous to those of the first passage, as described above, including preferred embodiments thereof and may include modifications which would be obvious to the skilled person.

The method of the invention may thus provide for a cell population comprising a considerable fraction of progenitor or stem cells, as defined in this disclosure, and the fraction of the said progenitor or stem cells can be increased by one or more passages of the prolonged culture of the primary liver cells. Typically, the population will comprise at least about 10%, e.g., at least about 20% of the said progenitor or stem cells, but the inventors found that typically higher proportions of the said progenitor or stem cells will be obtained, e.g., at least 30%, at least 40%, at least 50%, at least 60%, at least 70%, at least 80%, or at least at least 90% or more. Moreover, the method may even yield a substantially homogeneous or homogeneous population of the said progenitor or stem cells. The fraction of the progenitor or stem cells can be evaluated by any appropriate standard method, e.g., by flow cytometry.

Maintaining the Obtained Cells

When a population comprising the liver-derived progenitor or stem cells of the invention is achieved by the methods of the invention, and possibly further enriched for the said progenitor or stem cells, the cell population may next be maintained and/or propagated in conditions that allow for growth and doubling of the said progenitor or stem cells without differentiation. Such conditions may be, e.g., the ones used for obtaining the progenitor or stem cells. A skilled person who is capable of assessing the presence or absence of cell differentiation may readily establish further conditions. This can advantageously increase the number of the progenitor or stem cells available for further use thereof.

The present inventors have realised that the primary or any other subsequent passage could be cryopreserved for further use, as generally known in the art for mammalian cells.

The present inventors have realised that the progenitor or stem cells of the invention that emerged in the primary cell culture substantially retain their proliferation capacity after freezing and thawing. The said cells may be stored as a frozen concentrated cell suspension, thawed, as generally done in the art, and re-plated in the same conditions as described elsewhere in this specification.

Progenitor or Stem Cells of the Invention

The present inventors realised that the cell population obtained upon culture and preferably also passaging of primary liver cells as described above comprises liver-derived progenitor or stem cells of the invention, which co-express (i.e., are positive for) at least one mesenchymal marker, esp. one, more than one, e.g., 2, 3 or 4, or all of the markers CD90, CD73, CD44, vimentin and α-smooth muscle actin (ASMA), with the hepatocyte marker albumin (ALB) and possibly with one or more other hepatic or hepatocyte markers, preferably one, more than one, or all CD29, alpha-fetoprotein (AFP), alpha-1 antitrypsin and/or MRP2 transporter.

In a more particular embodiment, the liver-derived progenitor or stem cells of the invention may co-express (i.e., are positive for) at least one mesenchymal marker, esp. one, more than one, e.g., 2, 3 or 4, or all of the markers CD90, CD73, CD44, vimentin and α-smooth muscle actin (ASMA), with the hepatocyte marker albumin (ALB) and possibly with one or more other hepatocyte markers, preferably one or both of alpha-1 antitrypsin and MRP2 transporter, and with at least one hepatic marker CD29 or alpha-fetoprotein (AFP).

Any said adult liver progenitor or stem cell may further express one, more than one, or all of the following molecules indicative of hepatocyte-like properties or function: G6P, CYP1B1, CYP3A4, HNF-4, TDO, TAT, GS, GGT, CK8, EAAT2. The said adult liver progenitor or stem cell may further be characterised by one, more than one, or all of the following: negative for at least the hematopoietic markers CD45 and CD34 and possibly also for one or more other hematopoietic markers, such as, e.g., CD105 & HLA-DR; negative for the cholangiocyte epithelial marker cytokeratin-19 (CK-19) and possibly for more epithelial markers; negative for at least the undifferentiated stem cell markers CD117 and Oct-4 and possibly also for one or more than one embryonic stem cell markers; low level expression of alpha-fetoprotein (AFP). Preferably, the said adult liver progenitor or stem cell may have mesenchymal-like morphology, in particular involving one, more than one or all of growth in monolayers, flattened form, broad cytoplasm and/or ovoid nuclei with one or two nucleoli.

Identification of particular cell surface molecules by their CD ("common determinant") designations is commonplace in the art. Other names or designations of molecules in the present application are also used as well established in the art. Further specification of particular molecules may be also found in the examples.

Wherein a cell is said to be positive for a particular marker, this means that a skilled person will conclude the presence or evidence of a distinct signal, e.g., antibody-detectable or detection possible by reverse transcription polymerase chain reaction, for that marker when carrying out the appropriate measurement, compared to suitable controls. Where the method allows for quantitative assessment of the marker, positive cells may on average generate a signal that is significantly different from the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

The expression of cell-specific markers can be detected using any suitable immunological technique known in the art, such as flow cytometry, immuno-cytochemistry or affinity adsorption, Western blot analysis, ELISA, etc., or by any suitable technique of measuring the quantity of the marker mRNA, e.g., Northern blot, semi-quantitative or quantitative RT-PCR, etc.

A skilled person will appreciate that the cell population obtained by the present method, which comprises the above progenitor or stem cells may be harvested (e.g., by suitable detachment technique) and optionally further enriched for cells displaying specific characteristics by methods generally known in the art (hence, such cells can be isolated from the said population). By means of illustration and not limitation, cells displaying one or more surface molecules characteristic of the progenitor or stem cells of the invention, e.g., one or more of the markers listed above, may be recognised by specific (labelled) antibodies or other recognition agents against such as markers and sorted out from cells not displaying such surface molecules, e.g., using fluorescence activated cell sorting or using affinity binding to, e.g., columns, beads or surfaces (panning). Any other ways of enrichment for the cells are also included in the invention.

In a further aspect, the present inventors have thus realised a novel, isolated progenitor or stem cell (a vertebrate, preferably a mammal, even more preferably a human cell), originated from adult liver, characterised in that it co-expresses (i.e., is positive for) at least one mesenchymal marker, esp. one, more than one, e.g., 2, 3, or 4, or all of the markers CD90, CD29, CD44, vimentin and α-smooth muscle actin (ASMA), with the hepatocyte marker albumin (ALB) and possibly with one or more other hepatocyte markers. The said adult liver progenitor or stem cell may further be characterised by one, more than one, or all of the following: negative for at least the hematopoietic markers CD45, CD34 and CD117 and possibly also for one or more other hematopoietic markers; negative for cytokeratin-19 (CK-19); mesenchymal-like morphology, in particular involving any or all of growth in monolayers, flattened form, broad cytoplasm and/or ovoid nuclei with one or two nucleoli.

Hence, in a particular embodiment (1), the isolated, liver-derived progenitor or stem cell co-expresses CD90, CD73, CD44, vimentin and α-smooth muscle actin (ASMA), with ALB. In a further embodiment (2), the liver-derived progenitor or stem cell co-expresses CD90, CD44, vimentin and α-smooth muscle actin (ASMA), with ALB and alpha-1 antitrypsin. In a further embodiment (3), the liver-derived progenitor or stem cell co-expresses CD90, CD73, CD44, vimentin and α-smooth muscle actin (ASMA), with ALB and MRP2. In another embodiment (4), the liver-derived progenitor or stem cell co-expresses CD90, CD44, vimentin and α-smooth muscle actin (ASMA), with ALB, alpha-1 antitrypsin and MRP2. In further embodiments (5), the liver-derived progenitor or stem cell of any of the above embodiments (1) to (4) further express CD29. In further embodiments (6), the liver-derived progenitor or stem cell of any of the above embodiments (1) to (4) further express alpha-fetoprotein. In further embodiments (7), the liver-derived progenitor or stem cell of any of the above embodiments (1) to (4) further express CD29 and alpha-fetoprotein.

In further embodiments (8), the liver-derived progenitor or stem cell of any of the above embodiments (1) to (7) are negative for CD45 and CD34. In further embodiments (9), the liver-derived progenitor or stem cell of any of the above embodiments (1) to (7) are negative for CD117 and Oct-4. In further embodiments (10), the liver-derived progenitor or stem cell of any of the above embodiments (1) to (7) are negative for CD45, CD34, CD117 and Oct-4.

In further embodiments (11), the liver-derived progenitor or stem cell of any of the above embodiments (1) to (10) are negative for CK19. In further embodiments (12), the liver-derived progenitor or stem cell of any of the above embodiments (1) to (10) are negative for CK7. In further embodiments (13), the liver-derived progenitor or stem cell of any of the above embodiments (1) to (10) are negative for CK19 and CK7.

In further embodiments (14), the liver-derived progenitor or stem cell of any of the above embodiments (1) to (13) show mesenchymal-like morphology, preferably involving any or all of growth in monolayers, flattened form, broad cytoplasm and/or ovoid nuclei with one or two nucleoli.

In further embodiments (15), the liver-derived progenitor or stem cell of any of the above embodiments (1) to (14) further express one, more than one, or all of the following molecules indicative of hepatocyte-like properties or function: G6P, CYP1B1, CYP3A4, HNF-4, TDO, TAT, GS, GGT, CK8, EAAT2.

In further embodiments (16), the liver-derived progenitor or stem cell of any of the above embodiments (1) to (15) further express one, more than one, or all of the following molecules: CD49e, CD13, CD54, major histocompatibility complex (MHC) class I (HLA-ABC).

In further embodiments (17), the liver-derived progenitor or stem cell of any of the above embodiments (1) to (16) are negative for one, more than one, or all of the following molecules: CD105, HLA-DR, CD133, CD49b, CD49f & CD140.

In further embodiments (18), the liver-derived progenitor or stem cell of any of the above embodiments (6) to (17) express low level expression of alpha-fetoprotein (AFP). Preferably, said low level corresponds essentially to the level of expression measured in normal hepatocytes. Preferably, it is less than the level of expression measured in the tumorigenic modified human liver cell line, e.g., HepG2.

The isolated, liver-derived progenitor or stem cell of the invention may preferably display stem cell characteristics, esp. it may typically display at least limited (and possibly substantially unlimited) self-renewal, i.e., ability to propagate without differentiation. By means of example and not limitation, the progenitor or stem cells of the invention may be so propagated for at least 4 passages, e.g., at least 6 passages, at least 10 passages, or at least 20 passages, at least 50 passages, or more.

In another aspect, the invention provides an isolated adult liver progenitor or stem cell, cell line thereof and/or a cell population comprising such, obtainable by or directly obtained using a method comprising: (a) disassociating, preferably by two-step collagenase method, adult liver or a part thereof from a subject, preferably a vertebrate, mammal and more preferably a human subject, to form a population of primary cells from the said adult liver or part thereof; (b) plating the primary cell population onto collagen type I coated substrate in Williams Medium E comprising foetal calf serum, preferably 10% (v/v), EGF, preferably 25 ng/ml, insulin, preferably 10 µg/ml, and dexamethasone, preferably 1 µM; (c) allowing adherence of cells from the primary cell population to the said substrate for 24 hours and thereafter exchanging the medium for fresh medium having composition as in (b); (d) culturing the cells in the said medium of (c) during two weeks (preferably 15 days); (e) exchanging the medium for DMEM comprising high glucose and FCS, preferably 10%, and further culturing the cells, whereby the progenitor or stem cells of the invention emerge and proliferate; (f) optionally and preferably, allowing the cells to become about 70% confluent and passaging the cells at least once and preferably at least two times, wherein the cells are plated onto the substrate as in (b) and cultured in a medium as in (e).

The step (a) may preferably include disassociation of the primary cells by passing the cells through at least a sieve having pore size of 0.25 mm, and preferably through a succession of sieves having gradually decreasing pore sizes down to 0.25 mm, e.g., as in example 1.

The medium of step (e) may preferably not comprise dexamethasone, insulin and EGF and in an embodiment. The medium may in a further embodiment not comprise any exogenously added growth factor.

In an aspect, the invention also relates to the above methods.

In a further aspect, the invention provides an isolated liver progenitor or stem cell, cell line thereof and/or a cell population comprising such, obtainable or directly obtained following the protocol set out in example 1.

In a further aspect, the present inventors have established a cell population (cell line) of adult human liver progenitor or stem cells using the methods of the invention, in particular as documented in example 1, and deposited the said isolated cell line on Feb. 20, 2006 under the Budapest Treaty with the Belgian Coordinated Collections of Microorganisms (BCCM) under accession number LMBP 6452CB (given by the International Depositary Authority; identification reference given by the depositor: ADHLSC). Accordingly, in an aspect the present invention relates to an isolated cell, cell line and cell population deposited with BCCM under accession number LMBP 6452CB (herein, the "LMBP 6452CB" cell line), sub-lines thereof including clonal sub-lines, and to progeny thereof, including differentiated progeny thereof, esp. hepatocytes or hepatocytes-like cells prepared therefrom, and to genetically or otherwise modified derivatives thereof.

A skilled person will appreciate that progenitor or stem cells, cell lines thereof and cell populations comprising such, obtainable according to the methods of the invention from adult human liver may have biological properties, esp. proliferation and differentiation capacity, cell morphology and/or marker expression, identical or analogous to the above deposited cell line, albeit they may be genetically different (due to normal genetic variation between humans). Accordingly, a human progenitor or stem cell or cell population, esp. liver derived, having biological properties identical or analogous to the deposited cell population is also encompassed in the present invention.

In a further aspect, the invention provides a cell population comprising the isolated adult liver progenitor or stem cells of the above characteristics, and optionally further modified, e.g., genetically modified. In an embodiment, the said cell population may comprise about 5% or more, e.g., about 10% or more of the said progenitor or stem cells, about 20% or more, about 30% or more, about 40% or more, about 50% or more, about 60% or more, about 70% or more, about 80% or more or about 90% or more of the progenitor or stem cells or is a substantially homogeneous or homogeneous population of the said progenitor or stem cells.

In a further aspect, the invention provides a cell line established by propagating the liver-derived progenitor or stem cells of the invention, optionally further modified, e.g., genetically modified. Such propagating may depart from one progenitor or stem cell (a clonal cell line) or from more than one cells.

In a yet further aspect, the invention provides an isolated adult liver progenitor or stem cell, cell line thereof and/or a cell population comprising such, obtainable by or directly obtained using the above described methods of the invention, including preferred embodiments thereof.

Figure 2A:
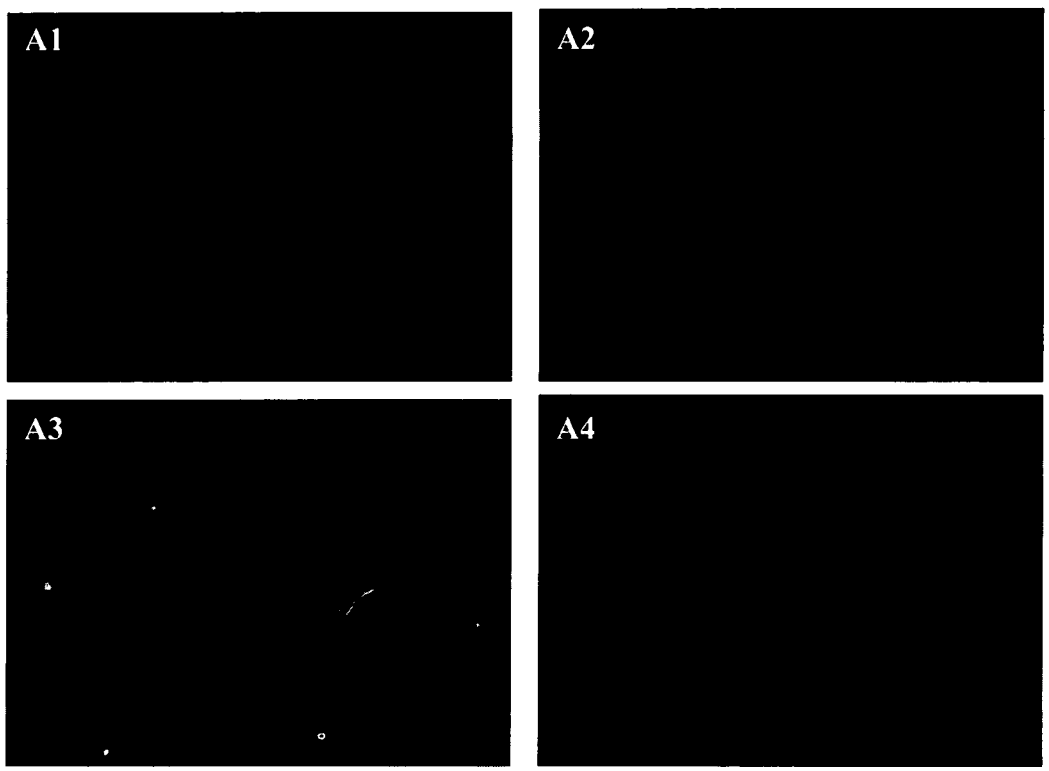
Figure 2B:
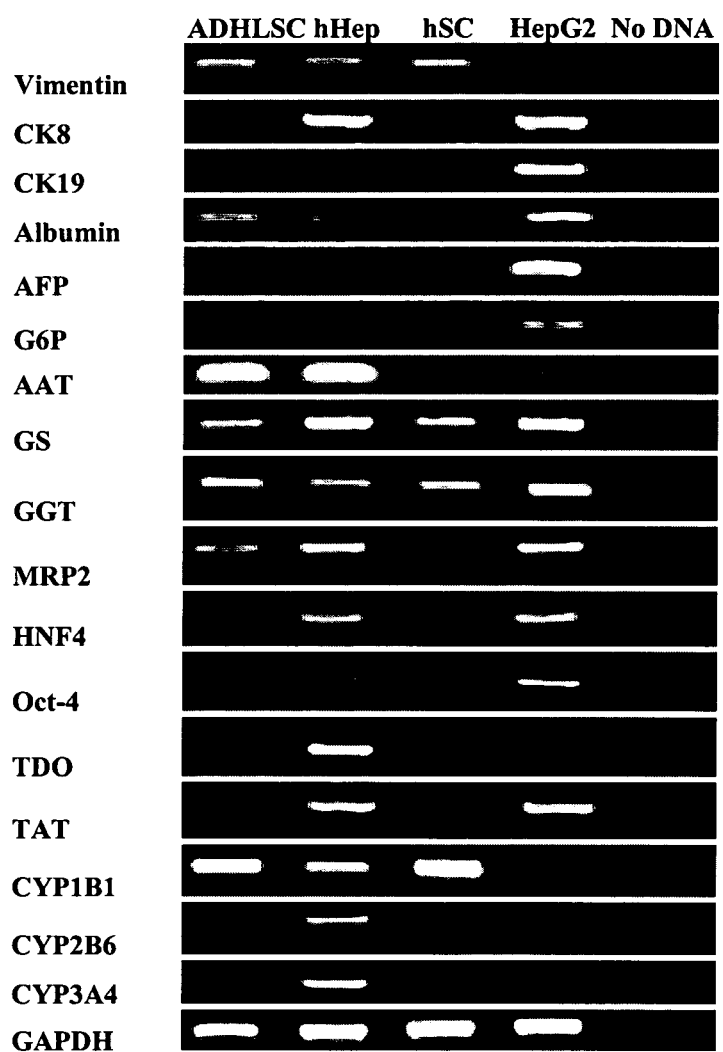

In a particular embodiment, the present invention thus provides a method for isolating a population of viable progenitor mesenchymal-like stem cells from adult normal (human) liver (FIG. 1). The stem cells were able to proliferate in a culture medium, and expressed markers of several liver cell types such as for instance albumin (hepatocytes), vimentin (stellate cells), alpha smooth muscle actin (ASMA) (FIG. 2A). They have no biliary phenotype, as shown by negative immunostaining and RT-PCR assays for cytokeratin 19 (FIG. 2B). When tested using flow cytometry, ADHLSC were negative for CD45, CD34 and CD1117 indicating their non-contamination by lymphohematopoietic lineage. In contrast, ADHLSC were positive for CD90, CD29 and CD44, markers for mesenchymal lineage.

Figure 3:
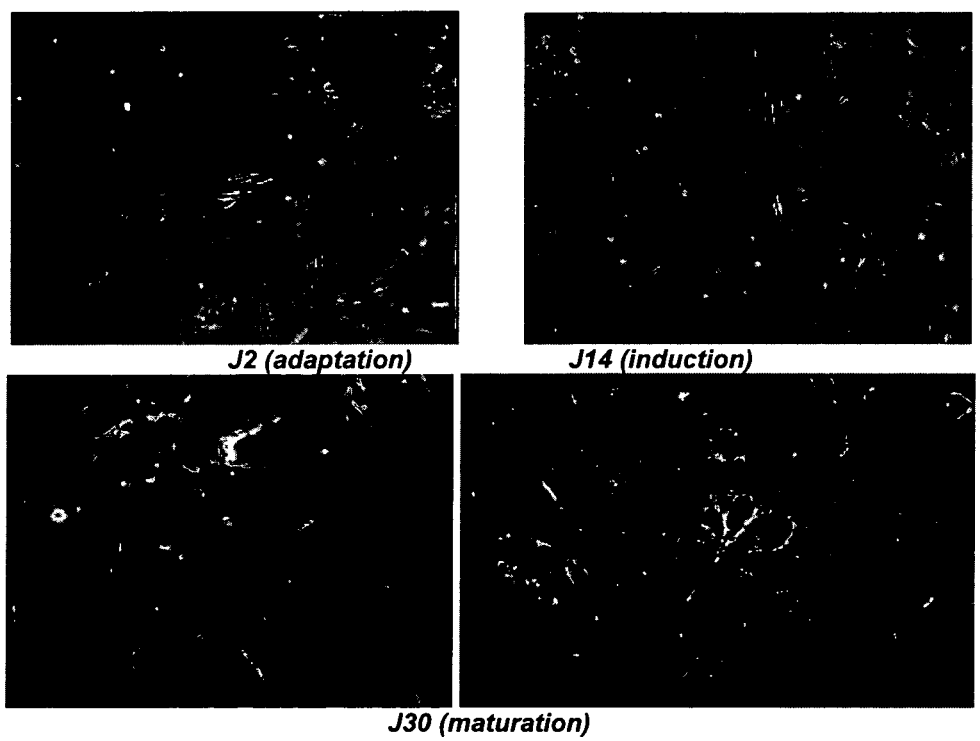

In an embodiment, the cells are able to retain their proliferation capacity after trypsin/EDTA treatment. Incubation in a defined medium allowed these cells to differentiate specifically into hepatocytes (FIG. 3). As further specificity criteria, they were not able to trans-differentiate into osteocytes or adipocytes, as would be observed using multipotent human mesenchymal bone marrow cells. Their proliferation capacity, and their liver specificity lead to an increased efficacy and safety for liver cell transplantation. Furthermore, because of their adult origin, these stem cells obviate the immunological, ethical and carcinogenic issues associated to embryonic cells.
Differentiation of the Progenitor or Stem Cells of the Invention In addition to detecting cell markers, study of cells' differentiation in vitro and/or in vivo may be informative.

The present inventors further realised that the liver-derived progenitor or stem cells obtained using the above methods may possess specific differentiation capacity. In particular, the cells can be differentiated into hepatocytes or hepatocyte-like cells. In a yet further embodiment, the cells do not differentiate to mesodermal (mesenchymal) cell types, such as, e.g., osteocytes, chondrocytes, myocytes, connective tissue cells, tendonocytes, adipocytes or stromal cells.

The isolated liver-derived progenitor or stem cell of the invention, cell lines thereof or cell populations comprising such (specifically mentioning, albeit of course not limited to, the LMBP 6452CB line), or progeny thereof, can be advantageously induced to differentiate to cells of the hepatocyte lineage, in particular hepatocytes or hepatocyte-like cells. Such differentiation can occur in vivo, or in vitro or ex vivo. Accordingly, the invention further provides a method for generation of hepatocytes or hepatocyte-like cells from the isolated progenitor or stem cell of the invention, and the resulting hepatocytes or hepatocyte-like cells.

In a particular embodiment, the liver-derived progenitor or stem cell of the invention is thus characterised by its ability to differentiate into hepatocytes or hepatocyte-like cells and lack of differentiation towards mesodermal cell types, such as, e.g., osteocytes and adipocytes.

As understood by those skilled in the art, the ability to differentiate towards a specific cell type or lack of such ability can be observed in vitro, ex vivo or in vivo. By means of example, in vitro or ex vivo differentiation can be assessed by exposing the cell to specific differentiation-inducing media as generally known in the art. Otherwise, differentiation can be assessed in vivo by following the fate of an introduced (e.g., transplanted, injected, or otherwise administered cell). A skilled person is able to recognise differentiation towards particular cell types by assessing phenotypic criteria including, but not limited to, cell morphology, marker protein expression, and/or activity of specific metabolic or other physiological pathways.

Differentiation into cells of the hepatocyte lineage may be advantageously effected in the presence of cytokines and growth factors, which can be liver-specific. By means of illustration, hepatocyte growth factor (HGF), or scatter factor, is a well-known cytokine that promotes differentiation to a hepatocyte phenotype. Similarly, a non-limiting list of further cytokines includes epidermal growth factor (EGF), basic FGF, insulin, nicotinamide, oncostatin M, dexamethasone, HDAC inhibitors (e.g., sodium butyrate), DMSO, Vitamin A, or matrix components such as heparin sulphate, which have also been implicated in differentiation towards hepatocytes. Protocols for inducing hepatocyte differentiation are generally known in the art and can be further optimised by a skilled person.

Identification and subsequent isolation of differentiated cells from their undifferentiated counterparts can be carried out by methods well known in the art. For example, cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, shape or the complexity of intracellular organelle distribution. Also contemplated are methods of identifying differentiated cells by their expression of specific marker proteins, such as cell-surface markers. Detection and isolation of these cells can be achieved, e.g., through flow cytometry, ELISA, and/or magnetic beads. Reverse-transcription polymerase chain reaction (RT-PCR) can also be used to monitor changes in gene expression in response to differentiation. In addition, whole genome analysis using microarray technology can be used to identify differentiated cells.
Genetic Modification of the Progenitor or Stem Cells of the Invention The said adult liver progenitor or stem cell may be further modified, e.g., genetically modified as described above. The invention further relates to the progeny, including differentiated progeny, of the adult liver progenitor or stem cell.

In an embodiment, to increase the replicative capacity of the obtained progenitor or stem cells of the invention, the cells can be telomerised as generally known in the art. A cell is described as "telomerised" if it has been genetically altered with a nucleic acid encoding a telomerase reverse transcriptase (TERT) of any species in such a manner that the TERT is transcribed and translated in the cell. The term also applies to progeny of the originally altered cell that have inherited the ability to express the TERT encoding region at an elevated level. The TERT encoding sequence is typically taken or adapted from a mammalian TERT gene, exemplified by human and mouse TERT, as indicated below. Cells may be telomerised by genetically altering them with a suitable vector, so that they express the telomerase catalytic component (TERT) at an elevated level. Particularly suitable is the catalytic component of human telomerase (hTERT), provided in WO 1998/14592. For some applications, other TERT sequences can be used. Other methods of immortalizing cells are also contemplated, such as genetically altering the cells with DNA encoding the SV40 large T antigen (U.S. Pat. No. 5,869,243, WO 1997/32972), infecting with Epstein Bar Virus, introducing oncogenes such as myc and/or ras, introducing viral replication genes such as adenovirus E1a, and fusing cells having the desired phenotype with an immortalized cell line. Transfection with oncogenes or oncovirus products is usually less suitable when the cells are to be used for therapeutic purposes.

In general, it might be preferred that the present progenitor or stem cells are not modified by telomerisation or other ways of immortalisation when the use of the said cells or progeny thereof, including differentiated progeny thereof, is contemplated in therapy, e.g., where such cells are to be introduced to human or animal, esp. human, body.

In the present invention, the obtained liver-derived progenitor or stem cells or progeny thereof may be stably or transiently transfected or transformed with a nucleic acid of interest prior to further use, e.g., in therapy or research, essentially as known in the art. Nucleic acid sequences of interest may include, but are not limited to, e.g., those encoding gene products which enhance the growth, differentiation and/or functioning of cell types useful in therapy, e.g., cell types derivable from the progenitor or stem cells of the invention, and particularly of hepatocytes or hepatocyte like cells, or to deliver a therapeutic gene to a site of administration or implantation of such cells.

By means of example and not limitation, the obtained progenitor or stem cells or progeny thereof may be modified to constitutively or inducibly over-express a polypeptide normally expressed by liver cells, esp. hepatocytes, but being defective or absent in a patient, this defect underlying a pathological state of the patient. Administration of the so modified cells may then restore production of the protein and thereby aid in treating the patient. For example, the progenitor or stem cells or progeny thereof may contain heterologous DNA encoding a metabolic protein such as ornithine transcarbamylase, arginosuccinate synthetase, arigininosuccinate lyase, arginase, carbamyl phosphate synthase, N-acetyl glutamate synthase, glutamine synthetase, glycogen synthetase, glucose-6-phosphatase, succinate dehydrogenase, glucokinase, pyruvate kinase, acetyl CoA carboxylase, fatty acid synthetase, alanine aminotransferase, glutamate dehydrogenase, ferritin, low density lipoprotein (LDL) receptor, P450 enzymes, and/or alcohol dehydrogenase. Alternatively, the cells may contain DNA encoding a secreted plasma protein such as albumin, transferrin, complement, component C3, $\alpha$2-macroglobulin, fibrinogen, Factor XIII, Factor IX, $\alpha$1-antitrypsin, or the like.

The liver is a centre of production for many secretory proteins. It is anatomically connected with the circulatory system in such a way that allows an efficient release of various proteins into the bloodstream. Therefore, genes encoding proteins that have systemic effects may be inserted into liver cells of the present invention as opposed to the specific cell types that normally produce them, especially if it is difficult to integrate genes into these cells. For example, a variety of hormone genes or specific antibody genes may be inserted into liver cells of the present invention for the secretion of their gene products into the circulation.

Conventional gene transfer methods are used to introduce nucleic acids into cells. The precise method used to introduce a gene is not critical to the invention. For example, physical methods for the introduction of DNA into cells include micro-injection and electroporation. Chemical methods such as co-precipitation with calcium phosphate and incorporation of DNA into liposomes are also standard methods of introducing DNA into mammalian cells. Viral transfection is also contemplated. DNA is introduced using standard vectors, such as those derived from murine and avian retroviruses (see, e.g., Gluzman et al., Viral Vectors, Cold Spring Harbour Laboratory, Cold Spring Harbour, N.Y., 1988). Standard recombinant DNA methods are well known in the art (see, e.g., Ausubel et al., Current Protocols in Molecular Biology, John Wiley & Sons, New York, 1989), and viral vectors for gene therapy have been developed and successfully used clinically (see, e.g., Rosenberg, et al., N. Engl. J. Med, 323: 370 1990).

Uses of the Progenitor or Stem Cells of the Invention

The isolated, liver originated progenitor or stem cell of the invention, cell lines thereof or populations comprising such can be used for different purposes (it is to be understood that the uses and applications in the following are broadly contemplated for any adult liver progenitor or stem cell as defined above, in particular for cells obtainable or directly obtained to using the above defined methods, cells displaying the above defined characteristics, as well as for the LMBP 6452CB cell line, in a particular embodiment, an isolated adult derived liver stem cell line, preferably an adult derived human liver stem cell line (ADHLSC); progeny thereof; or genetically modified derivatives thereof, including but not limited to:

liver cell transplantation in order to treat liver metabolic deficiencies, liver degenerative diseases or fulminant liver failure, using the isolated progenitor or stem cell or population thereof according to the invention, the preparation of bio-artificial liver devices using the isolated progenitor or stem cell or population thereof according to the invention, the preparation of animal models of human liver diseases thanks to transplantation of isolated progenitor or stem cell or population thereof according to the invention in animals, the preparation of in vitro and animal models of toxicology, pharmacology using the isolated progenitor or stem cell or population thereof according to the invention, testing new drugs on the isolated progenitor or stem cell or population thereof according to the invention, including antiviral drugs for human hepatitis viruses.

Figure 4:
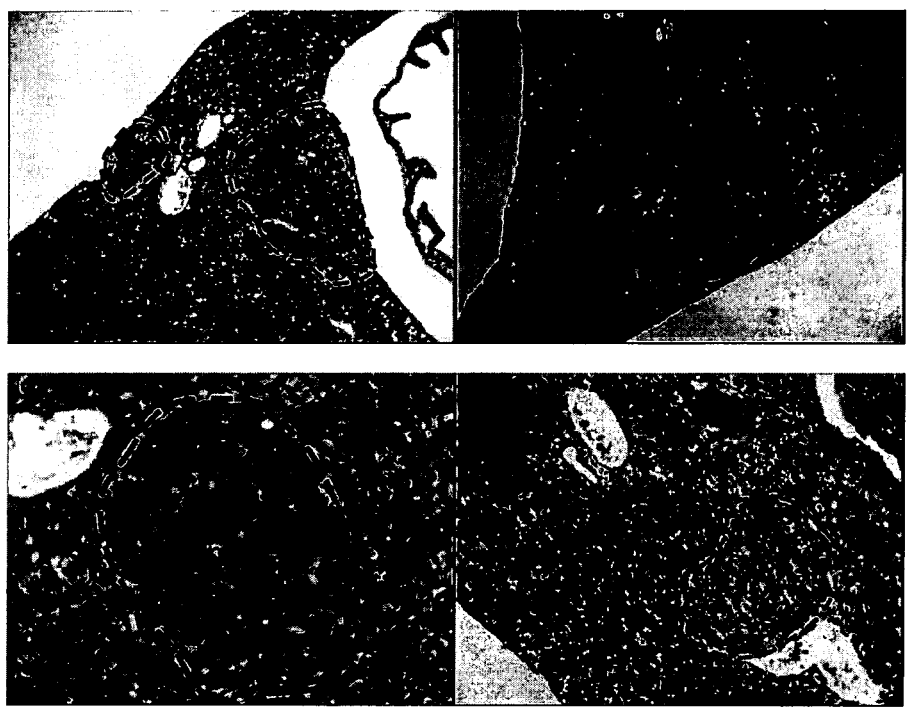
FIG. 4 shows several images of hematoxylin and eosin staining in chimeric liver of uPA/SCID mice transplanted with undifferentiated ADHLSC cells, as detailed in example 1, demonstrating that these cells become differentiated hepatocytes.
Figure 5:
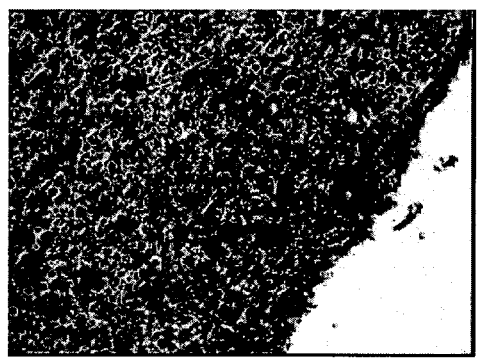
FIG. 5 shows several images of staining for human albumin unveiling the human origin of hepatocytes like population observed 10 weeks post-transplantation as in example 1 with undifferentiated ADHLSC.
Figure 5:
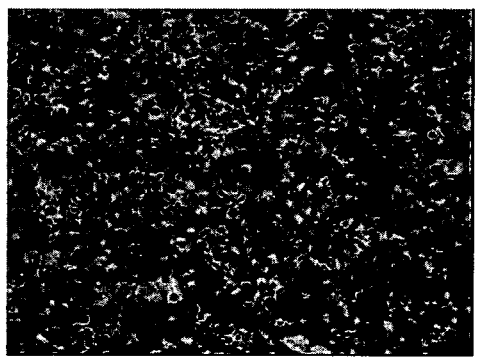
Figure 5:
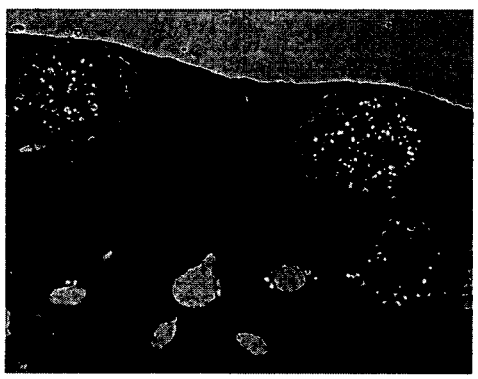

For example, the analysis of the livers of uPA$^{+/+}$-SCID and SCID mice intrasplenically transplanted with ADHLSC (LMBP 6452CB line), demonstrated that these cells were able to engraft and to differentiate into mature hepatocytes (FIGS. 4 & 5). Furthermore, human albumin was detected in the serum of these transplanted mice 10 weeks post-transplantation whereas no alpha-fetoprotein levels were detected.

According to the present invention the liver progenitor or stem cells (specifically mentioning, albeit of course not limited to, the LMBP 6452CB line) can be used for the transplantation in inborn error of metabolism, for the transplantation in animal models of liver failure or for the transplantation for animal models of human viral hepatitis. The present cells can therefore be used in the treatment of liver associated diseases including but not limited to liver failure, hepatitis, inborn errors of metabolism.

In an exemplary embodiment, as shown in example 1, the inventors demonstrate that human liver progenitor or stem cells of the invention, when administered via intrasplenic injection to an immuno-deficient mammal, more preferably a rodent, esp. a mouse or rat, retain their proliferation capacity and engraft within the host liver. Accordingly, in an embodiment, a cell population comprising liver progenitor or stem cells of the invention, preferably of human origin (specifically mentioning, albeit of course not limited to, the LMBP6452CB line), is introduced, e.g., injected, and allowed to engraft in a mammal genetically or chemically made immuno-deficient, to obtain an animal model. Preferably, such population may comprise at least $2 \times 10^6$ cells of the invention. A skilled person will appreciate other ways of administering the cell population of the invention to induce liver engraftment of the said adult-derived liver progenitor or stem cells.

As detailed in example 1, the engrafted cells did not overproliferate, thus underscoring their advantages in cell transplantation in humans or other animals, preferably mammals.

The present invention also encompasses the use of the isolated progenitor or stem cell or population thereof according to the invention (specifically mentioning, albeit of course not limited to, the LMBP 6452CB line), for the following purposes:

- liver progenitor or stem cell transplantation in order to treat liver based inborn, metabolic deficiencies: Non exhaustive examples of such diseases include phenylketonuria and other aminoacidopathies, haemophilia and other clotting factor deficiencies, familial hypercholesterolemia and other lipid metabolism disorders, urea cycle disorders, glycogenosis, galactosemia, fructosemia, tyrosinemia, protein and carbohydrate metabolism deficiencies, organic aciduria, mitochondrial diseases, peroxysomal and lysosomal disorders, protein synthesis abnormalities, defects of liver cell transporters, defect of glycosylation and the like,
- transplantation of the liver progenitor or stem cell according to the invention to treat acquired progressive liver degenerative diseases,
- use of the liver progenitor or stem cell according to the invention to treat fulminant liver failure and acute or chronic liver failure,
- use of the liver progenitor or stem cell according to the invention in bio-artificial liver devices and liver assist devices,
- animal models of human liver diseases thanks to transplantation of the liver progenitor or stem cell according to the invention in small and large animals,
- the preparation of animal models of human hepatotropic virus infections (HBV, HAV, HCV, HEV, HDV, . . . ) to study natural history, transmission, resistance, effects of treatment, use of antiviral drugs or any research using transplanted the liver progenitor or stem cell according to the invention,
- the preparation of in vitro and animal models of toxicology, pharmacology and pharmacogenetics using the liver progenitor or stem cell according to the invention,
- the testing new drugs on the liver progenitor or stem cell according to the invention,
- gene therapy, by inserting viral sequences in the liver progenitor or stem cell according to the invention which can then be expanded in vitro,
- animal models to study human liver cell metabolism,
- tolerance of allogeneic cells thanks to the use of the liver progenitor or stem cell according to the invention, and/or
- use of the liver progenitor or stem cell according to the invention to avoid, prevent or treat liver or liver cell allograft rejection.

The present progenitor or stem cells or progeny thereof, including differentiated progeny, may in an aspect of the invention be intended for therapeutic applications, e.g., for tissue engineering and cell therapy.

A skilled person will appreciate that the herein detailed uses may involve the use of the progenitor or stem cells, cell lines thereof, cell populations comprising such, as well as the use of progeny thereof, including differentiated progeny, esp. hepatocytes or hepatocyte-like cells, or genetically modified derivatives thereof.

As noted above, the liver originated progenitor or stem cells of the invention, cell lines thereof or cell populations comprising such (specifically mentioning, albeit of course not limited to, the LMBP 6452CB line), or progeny thereof, optionally genetically modified, can be used in cell replacement therapies. The cells can be administered to a tissue of interest in a subject to supplement functioning cells or replace cells, which have lost function. Alternatively, methods of providing differentiated cells, particularly hepatocytes or hepatocyte-like cells, are also contemplated, wherein progenitor or stem cells are differentiated in the presence of differentiation factors, isolated, and administered in a subject.

Disease states or deficiencies typified by loss of liver mass and/or function, and that could benefit from progenitor or stem cells of the invention include those listed above, and further include but are not limited to Alagille syndrome, alcoholic liver disease (alcohol-induced cirrhosis), $\alpha$1-antitrypsin deficiency (all phenotypes), hyperlipidemias and other lipid metabolism disorders, autoimmune hepatitis, Budd-Chiari syndrome, biliary atresia, progressive familial cholestasis type II, II and III, cancer of the liver, Caroli Disease, Crigler-Najjar syndrome, fructosemia, galactosemia, carbohydrate deficient glycosylation defects, other carbohydrate metabolism disorders, Refsum disease and other peroxysomal diseases, Niemann Pick disease, Wolman disease and other lysosomal disorders, tyrosinemia, triple H, and other amino acid metabolic disorders, Dubin-Johnson syndrome, fatty liver (non alcoholi steato hepatitis), Gilbert Syndrome, Glycogen Storage Disease I and III, hemochromatosis, hepatitis A-G, porphyria, primary biliary cirrhosis, sclerosing cholangitis, tyrosinemia, clotting factor deficiencies, hemophilia B, phenylketonuria, Wilson's Disease, fulminant liver failure, post hepatectomy liver failure, mitochondrial respiratory chain diseases. In addition, the cells can also be used to treat acquired liver disorders due to viral infections.

Accordingly, in an aspect are provided adult liver progenitor or stem cells of the invention, cell lines thereof or cell populations comprising such (specifically mentioning, albeit not limited to, the LMBP 6452CB line), or progeny thereof including differentiated progeny, esp. hepatocytes or hepatocyte like cells, optionally genetically modified as detailed above, for use in therapy and/or use thereof for the manufacture of a medicament for the treatment of liver diseases. Such diseases may include disorders affecting liver tissue, diseases affecting the hepatocyte viability and/or function are specifically contemplated, and may represent, e.g., inborn errors, the effect of a disease condition, the effect of trauma, toxic effects, viral infections, etc. Liver diseases listed in the present specification are specifically contemplated. Administration of the cells according to the invention can lead to tissue reconstitution or regeneration in the subject. The cells are administered in a manner that permits them to graft or migrate to the intended tissue site and reconstitute or regenerate the functionally deficient area.

Another aspect of the invention is a method for preventing and/or treating a liver disease, comprising administration of adult liver progenitor or stem cells of the invention, cell lines thereof or cell populations comprising such (specifically mentioning, albeit not limited to, the LMBP 6452CB line), or progeny thereof including differentiated progeny, esp. hepatocytes or hepatocyte like cells, optionally genetically modified, to a subject, esp. human, in need of such treatment. Such administration is typically in therapeutically effective amount, i.e., generally an amount which provides a desired local or systemic effect and performance.

In a further aspect, the invention relates to a pharmaceutical composition comprising the adult liver progenitor or stem cells of the invention, cell lines thereof or a cell population comprising such (specifically mentioning, albeit not limited to, the LMBP 6452CB line), or progeny thereof including differentiated progeny, esp. hepatocytes or hepatocyte like cells, optionally genetically modified as above.

By means of example and not limitation, the isolated liver progenitor or stem cells of the invention, cell lines thereof or cell populations comprising such (specifically mentioning, albeit of course not limited to, the LMBP 6452CB line), or progeny thereof can be advantageously administered via injection (encompassing also catheter administration) or implantation, e.g. localised injection, systemic injection, intrasplenic injection (see also Gupta et al., Seminars in Liver Disease 12: 321, 1992), injection to a portal vein, injection to liver pulp, e.g., beneath the liver capsule, parenteral administration, or intrauterine injection into an embryo or foetus.

In a preferred embodiment, the liver originated progenitor or stem cells of the invention, cell lines thereof or cell populations comprising such (specifically mentioning, albeit of course not limited to, the LMBP 6452CB line), or progeny thereof, optionally genetically modified, can be used for tissue engineering and cell therapy via liver cell transplantation (LCT). Liver cell transplantation, and liver stem cell transplantation (LSCT) refers to the technique of infusing mature hepatocytes or liver progenitor cells, including the cells of the invention, in any way leading to hepatic access and engraftment of the cells, preferably via the portal vein, but also by direct hepatic injection, or by intrasplenic injection.

For example, the cells may be provided as a cell suspension in any preservation medium, preferably containing human albumin, after isolation procedure or after thawing following cryopreservation.

In an embodiment, the present invention contemplates using a patient's own liver tissue to isolate the progenitor or stem cells of the invention. Such cells would be autologous to the patient and could be readily administered to the patient. Moreover, if the patient contained a genetic defect underlying a particular pathological condition, such defect could be averted by genetically manipulating the obtained cells.

In another embodiment, the progenitor or stem cells of the invention may be isolated from tissue which is not patient's own. Where administration of such cells to a patient is contemplated, it may be preferable that the liver tissue subjected to the method of the present invention to obtain the progenitor or stem cells, is selected such as to maximise, at least within achievable limits, the tissue compatibility between the patient and the administered cells, thereby reducing the chance of rejection of the administered cells by patient's immune system (e.g., graft vs. host rejection).

The ability of the immune system to differentiate self from non-self is to a large extent determined by products of the major histocompatibility complex (MHC), whose genes are on chromosome 6 and belong to the immunoglobin gene super-family. Class I MHC products consist of HLA-A, HLA-B and HLA-C; these have a wide distribution and are present on the surface of essentially all nucleated cells and on platelets. Class II MHC products consist of HLA-D, HLA-DR, HLA-DP, and HLA-DQ; they have a more limited distribution, including on B cells, macrophages, dendritic cells, Langerhans' cells, and activated (but not resting) T cells.

The HLA loci are generally multi-allelic, e.g., using specific antibodies, at least 26 HLA-A alleles, 59 HLA-B alleles, 10 HLA-C alleles, 26 HLA-D alleles, 22 HLA-DR alleles, nine HLA-DQ alleles and six HLA-DP alleles can be recognized. Because HLA loci are closely linked, the HLA antigens may also be present as conserved haplotypes.

A subject in need of therapy with cells of the present invention may be screened for the presence of anti-HLA antibodies and for his HLA genotype and/or phenotype (e.g., on lymphocytes; e.g., using serological methods or genetic DNA analysis). Progenitor or stem cells obtainable according to the present invention, or the source liver tissue or the donor thereof, may be typically tested for their HLA phenotype and/or genotype and suitable tissues or cells selected for administration, which have either identical HLA haplotypes to the patient, or which have the most HLA antigen alleles common to the patient and none or the least of HLA antigens to which the patient contains pre-existing anti-HLA antibodies. The probability that the transplanted cells will be successfully accepted increases with the number of identical HLA antigens. A skilled person will understand the further variations of these considerations.

Other ways of obtaining MHC profile resembling the patient's are also contemplated, e.g., genetic manipulation of the obtained progenitor or stem cells of the invention or progeny thereof.

If the cells are derived from heterologous (i.e., non-autologous) source, concomitant immunosuppression therapy may be typically administered, e.g., using immunosuppressive agents, such as cyclosporine or tacrolimus (FK506). Alternatively, the cells can be encapsulated in a membrane which permits exchange of fluids but prevents cell/cell contact. Transplantation of microencapsulated cells is known in the art, e.g., Balladur et al., 1995, Surgery 117:189-194; and Dixit et al., 1992, Cell Transplantation 1:275-279. Preferably, the cells may be autologous, or displaying a close HLA match as explained.

In another preferred embodiment, the adult liver or part thereof is from a non-human animal subject, preferably a non-human mammal subject. Progenitor or stem cells or cell lines, or progeny thereof, derived according to the invention from livers of non-human animal or non-human mammal subjects can be advantageously used, e.g., in research and in the therapy of liver disease in members of the same, related or other non-human animal or non-human mammal species, or even in the therapy of human patients suffering from liver disease (e.g., xenotransplantation, bio-artificial liver devices comprising non-human animal or non-human mammal cells). By means of example and not limitation, particularly suitable non-human mammal cells for use in human therapy may originate from pigs.

An issue concerning the therapeutic use of the progenitor or stem cells of the invention is the quantity of cells necessary to achieve an optimal effect. Doses for administration may be variable, may include an initial administration followed by subsequent administrations; and can be ascertained by the skilled artisan armed with the present disclosure. Typically, the administered dose or doses will provide for a therapeutically effective amount of the cells, i.e., one achieving the desired local or systemic effect and performance.

In current human studies of autologous mononuclear bone marrow cells, empirical doses ranging from 1 to $4\times10^7$ cells have been used with encouraging results. However, different scenarios may require optimisation of the amount of administered cells. Thus, the quantity of cells to be administered will vary for the subject being treated. In a preferred embodiment, between $10^2$ to $10^9$, or between $10^3$ to $10^9$, or between $10^4$ to $10^9$, such as between $10^4$ and $10^8$, or between $10^5$ and $10^7$, e.g., about $1\times10^5$, about $5\times10^5$, about $1\times10^6$, about $5\times10^6$, about $1\times10^7$, or about $2\times10^7$, about $3\times10^7$, about $4\times10^7$, about $5\times10^7$, about $6\times10^7$, about $7\times10^7$, about $8\times10^7$, about $9\times10^7$, or about $1\times10^8$, cells can be administered to a human subject. However, the precise determination of a therapeutically effective dose may be based on factors individual to each patient, including their size, age, size tissue damage, and amount of time since the damage occurred, and can be readily ascertained by those skilled in the art from this disclosure and the knowledge in the art.

Preferably, purity of a cell population comprising the progenitor or stem cells of the invention for administration may be about 50 to about 55%, about 55 to about 60%, and about 65 to about 70%. More preferably the purity may be about 70 to about 75%, about 75 to about 80%, about 80% to about 85%; and most preferably the purity may be about 85 to about 90%, about 90 to about 95%, and about 95 to about 100%. Purity of the stem cells can be determined, e.g., according to the cell surface marker profile within a cell population. Dosages can be readily adjusted by those skilled in the art (e.g., lower purity may require an increase in dosage).

The skilled artisan can readily determine the amount of cells and optional additives, vehicles, and/or carrier in compositions to be administered in methods of the invention. Typically, any additives (in addition to the active progenitor or stem cell(s) and/or cytokine(s)) may be present in an amount of 0.001 to 50% (w/w or w/v) solution in phosphate buffered saline, and the active ingredient may be typically present in the order of micrograms to milligrams, such as about 0.0001 to about 5% (w/w or w/v), preferably about 0.0001 to about 1%, most preferably about 0.0001 to about 0.05% or about 0.001 to about 20%, preferably about 0.01 to about 10%, and most preferably about 0.05 to about 5%.

When administering a therapeutic composition of the present invention, it may generally be formulated in a unit dosage injectable form (e.g., solution, suspension, dispersion, emulsion). The pharmaceutical formulations suitable for injection include sterile aqueous solutions and dispersions. As used herein, the solutions or dispersions include a pharmaceutically acceptable carrier or diluent in which the cells of the invention remain viable. The carrier can be a pharmaceutically acceptable solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like.

In many cases, it will be desirable to include isotonic agents to ensure viability of the cells, for example, sugars, sodium chloride, and the like. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

To potentially increase cell survival when introducing the progenitor or stem cells or differentiated progeny of interest thereof into a subject in need thereof, may be to incorporate the said cells into a biopolymer or synthetic polymer. Examples of suitable biopolymers include, but are not limited to, fibronectin, fibrin, fibrinogen, thrombin, collagen, and proteoglycans. This could be constructed with or without included cytokines, growth factors, differentiation factors or nucleic acid expression constructs, etc. Such biopolymers could be, e.g., in suspension or could for a three-dimensional gel with the cells embedded there within. Such polymers can be preferably biodegradable.

Prolonged absorption of the injectable pharmaceutical form can be brought about by the use of agents delaying absorption, for example, aluminum monostearate and gelatin. According to the present invention, however, any vehicle, diluent, or additive used would have to be compatible with the progenitor or stem cells.

Sterile injectable solutions can be prepared by incorporating the cells utilized in practicing the present invention in the required amount of the appropriate solvent with various amounts of the other ingredients, as desired.

Such compositions may further be in admixture with a suitable carrier, diluent, or excipient such as sterile water, physiological saline, glucose, dextrose, or the like. The compositions can contain auxiliary substances such as wetting or emulsifying agents, pH buffering agents, gelling or viscosity enhancing additives, preservatives, flavouring agents, colours, and the like, depending upon the route of administration and the preparation desired.

Standard texts, such as "Remington's pharmaceutical science", 17th edition, 1985, incorporated herein by reference, may be consulted to prepare suitable preparations, without undue experimentation.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The point is to use an amount, which will achieve the selected viscosity. Viscous compositions are normally prepared from solutions by the addition of such thickening agents.

Further Uses of the Progenitor or Stem Cells of the Invention

Further uses of the progenitor or stem cells of the invention, cell lines thereof or cell populations comprising such (specifically mentioning, albeit not limited to, the LMBP 6452CB line), or progeny thereof including differentiated progeny, esp. hepatocytes or hepatocyte like cells, optionally genetically modified, are contemplated below.

Thus, the progenitor or stem cells or differentiated derivatives thereof, esp. hepatocytes or hepatocyte like cells, can be used to detect cellular responses (e.g., toxicity) to bioactive (biologic or pharmacologic) agents, comprising contacting a culture of cells, or the differentiated derivatives thereof, with one or more biologic or pharmacologic agents, identifying one or more cellular response to the one or more biologic or pharmacologic agents, and comparing the cellular responses of the cell cultures to the cellular responses of control cultures. Such responses can be determined by monitoring the activities of molecules such as, but not limited to, alkaline phosphatase, cytochrome P450, urea pathway enzymes, among others.

Further, cytokines, chemokines, pharmaceutical compositions and growth factors, for example, can be screened using the progenitor or stem cell of the invention or differentiated derivatives thereof, esp. hepatocytes or hepatocyte like cells, to more clearly elucidate their effects on differentiation and function of such cells.

The invention also envisions a tissue-engineered organ, or portion, or specific section thereof, a tissue engineered device comprising a tissue of interest and optionally, cytokines, growth factors, or differentiation factors, wherein the cells of the invention are used to generate tissues, esp. liver tissue, esp. tissues comprising hepatocytes. Tissue-engineered organs can be used with a biocompatible scaffold to support cell growth in a three-dimensional configuration, which can be biodegradable. Tissue-engineered organs generated from the stem cells of the present invention can be implanted into a subject in need of a replacement organ, portion, or specific section thereof. The present invention also envisions the use of the stem cells or cells differentiated therefrom as part of a bioreactor, e.g., a liver assist device.

Organs, portions, or sections derived from the stem cells of the invention can be implanted into a host. The transplantation can be autologous, such that the donor of the stem cells from which organ or organ units are derived is the recipient of the engineered tissue. The transplantation can be heterologous, such that the donor of the stem cells from which organ or organ units are derived is not that of the recipient of the engineered-tissue. Once transferred into a host, the tissue-engineered organs can recapitulate the function and architecture of the native host tissue. The tissue-engineered organs will benefit subjects in a wide variety of applications, including the treatment of cancer and other disease disclosed herein, congenital defects, or damage due to surgical resection.

As a tool for the drug testing and development process, the liver cells and their progeny could be used to assess changes in gene expression patterns caused by drugs being considered for development. The changes in gene expression pattern from potential drugs could be compared with those caused by drugs known to affect the liver. This would allow a pharmaceutical company to screen compounds for their effect on the liver earlier in the development process, saving time and money. The full lineage of liver cells, from progenitors to mature cells, could also be used to test drugs for toxicity to the liver and to study how the drug is metabolized. Currently, pharmaceutical companies have difficulty obtaining a consistent supply of liver cells for toxicity testing. The methods and cells of the present invention answer this need.

Further, the adult liver progenitor or stem cells of the invention or progeny thereof including differentiated progeny, esp. hepatocytes or hepatocyte like cells are useful as biological components of detoxification devices such as liver perfusion or liver assist devices.

A conventional liver assist device includes a rigid, plastic outer shell and hollow semi-permeable membrane fibres which are seeded with stem cells or differentiated hepatocytes or derived from the stem cells. The fibres may be treated with collagen, lectin, laminin, or fibronectin, for the attachment of cells or left untreated. Bodily fluid is perfused through the device for detoxification according to well known procedures and then returned to the patient. An example of an LAD suitable for the cells of the present invention is described in International Patent Publication Serial Number PCT US00/15524.

The adult liver progenitor or stem cells of the invention or progeny thereof can be differentiated in vitro and further used in place of mature hepatocytes in "ADMET" administration, distribution, metabolism, elimination and toxicology) or cytotoxicity tests.

Hepatocytes or hepatocyte-like cells obtained by differentiating the adult liver progenitor or stem cells of the invention or progeny thereof may provide an in vitro model for liver development study, liver cell metabolism or liver cell biology; and for screen differentiating, proliferative or toxic molecules. Further contemplating genetic manipulation of such cells, they can be used to study genes implicated in liver development, liver cell metabolism or biology.

The invention will now be illustrated by means of the following examples, which do not limit the scope of the invention in any way.

EXAMPLE 1

Liver Cell Isolation Procedure

Human liver cells were obtained from the whole liver or liver segments originating from healthy cadaveric or non heart beating donors. Cells were isolated after the gross clamp time (e.g., between 6 and 12 hours after gross clamp time) while livers were kept on ice in a University of Wisconsin medium until the perfusion. Hepatocytes were isolated using a classic 2-step perfusion technique {Seglen, 1976} {Stephenne, 2005}. Liver tissue was sequentially perfused by the apparent blood vessels with an EGTA solution (Earl's Balanced Salt Solution without $Ca^{++}$ and $Mg^{++}$, 0.5 mM EGTA, 5 mM Hepes, 2 mg/l gentamicin, and 100,000 IU/I penicillin G) and a digestion enzyme solution for 9 to 12 minutes each at 37° C. The digestion solution (EBSS with $Ca^{++}$ and $Mg^{++}$, 5 mM Hepes, 2 mg/l gentamicin, and 100,000 IU/I penicillin G) included 0.9 mg/ml of collagenase P and 0.03 mg/ml of soybean trypsin inhibitor. The liver capsule was incised and the hepatocytes were released by gentle shaking. Digestion was stopped with ice-cold wash medium (medium M199, 5 mM Hepes, 2 mg/l gentamicin and 100,000 IU/I penicillin G), containing 0.03 mg/ml of soybean trypsin inhibitor and 100 ml/l of human plasma. The cells were filtered and rinsed through 4 metal sieves of respectively, 4.5 mm, 1 mm, 0.5 mm, and 0.25 mm of pore size. Cells were washed 3 times by centrifugation at 1200 rpm for 3 minutes in a cold M199 wash medium.

Primary Cell Culture

Single cell suspensions were resuspended in Williams' E medium (Invitrogen) supplemented with 10% fetal calf serum (FCS) (Perbio, Hyclone), 25 ng/ml EGF (Peprotech), 10 µg/ml insulin, 1 µM dexamethazone and 1% penicillin/streptomycin (P/S) (invitrogen). The cells were plated on rat tail collagen I (BD Biosciences)—coated flasks or plates (e.g., 6-well plates) (Greiner Bio-one) and cultured at 37° C. in a fully humidified atmosphere containing 5% $CO_2$. After 24 hours, medium was changed in order to eliminate the non-adherent cells and thereafter renewed every three days. During two weeks, the culture was followed microscopically everyday and culture medium was analyzed every three days. Culture medium was then switched to DMEM with high glucose concentrations (invitrogen) supplemented with 10% FCS (Perbio, Hyclone) and 1% P/S (Invitrogen) in order to accelerate the elimination of adult hepatocytes. A cell type with mesenchymal-like morphology then spontaneously emerged, proliferated and filled the empty space in the well plate as confirmed by phase contrast microscopy. These cells appeared between day 15 and 20 of the culture and presented a flattened form, broad cytoplasm and ovoid nuclei with one or two nucleoli (FIG. 1). When reaching 70% confluence, cells were lifted with 0.25% trypsin and 1 mM EDTA and re-plated at the desired concentration. The analysis of cell suspension using flow cytometry showed that the population became homogenous after passage 2. For each passage, cell suspension was also analyzed using RT-PCR, and immunofluorescence.

Characterization of the Cells

In order to avoid the possible contamination by other cell types, immunocytochemistry was performed to study the phenotype of these cells. Because of their hepatic origin, expression of specific markers such as albumin has been analyzed in paraformaldehyde-fixed cells. As shown in FIG. 2, albumin which is exclusively expressed in hepatocytes, was detected both using monoclonal (Sigma clone HAS-111) or polyclonal (Chemicon) antibodies. In parallel, expression of mesenchymal cell markers has also been evaluated demonstrating that these cells are immuno-positive for vimentin and alpha smooth muscle actin (FIG. 2). So far the phenotypic characteristics have been studied over 7 passages with great stability.

Cell Differentiation:

Cells were seeded at a density of $0.5\text{-}1\times10^4/cm^2$ in 6 well plates coated with rat-tail collagen type I in DMEM supplemented with FCS and P/S. Culture medium was switched 24 hours later to Iscove's modified Dulbecco's medium (IMDM) (Invitrogen). For induction, the cells were incubated for 2 weeks with induction medium containing IMDM supplemented with 20 ng/ml HGF (Biosource), 10 ng/ml bFGF (Peprotech) and 0.61 g/l nicotinamide (Sigma). Thereafter, cells were incubated with maturation medium containing IMDM supplemented with 20 ng/ml oncostatin M (Sigma), 1 µM dexamethasone (Sigma), 50 mg/ml ITS (insulin, transferrin, selenium) (Invitrogen). For induction and maturation steps, medium was changed and analyzed every 3 days. After exposure to these cocktails, cells started to lose their sharp edges, were progressively shrunk and lost their initial morphology to adopt a polygonal shape (FIG. 3).

Flow Cytometry:

Cells were collected after centrifugation at 1200 rpm for 5 min and re-suspended at a concentration of 500 to 1000/µl in PBS. Cells were then incubated for 30 minutes at 4° C. with antibodies. The corresponding control isotypes were used for evaluation of nonspecific binding of monoclonal antibodies. Cells were then washed and resuspended in Isoton® (Beckham Coulter) for reading with a Beckham Coulter Flow Cytometer.

RT-PCR

Total RNA was extracted from cells grown in 6 wells-plates using the TriPure isolation reagent (Roche) and cDNA was generated using the reverse transcription kit, according to the manufacturer's instructions. PCR amplifications were performed using polymerase elongase in a final volume of 25 µl and appropriate primers. Samples were thereafter electrophoresed on a 1% agarose gel and nucleic acids were visualized by ethidium bromide staining.

Immunofluorescence

For immunostaining, cells grown on rat tail collagen I—coated 12 mm round glass coverslips were fixed with paraformaldehyde 4% (v/v) for 15 min at room temperature and permeabilised thereafter with 1% Triton X100 (v/v) in TBS (Tris-HCl 50 mM, NaCl 150 mM, pH 7.4) during 15 min. Non-specific immunostaining was prevented by 1 h incubation in a TBS solution containing 3% non-fat dry milk at 37° C. Cells were then successively incubated in the same solution for 1 h at room temperature with primary antibodies, rinsed 5 times with TBS and for 1 h with secondary antibodies (1/500). Nuclei were stained during 30 min with the nuclear dye DAPI (1/5,000). After 3 rinses, preparations were mounted in Fluoprep medium (BioMerieux, Brussels, Belgium) and examined using an Olympus IX70 inverted microscope coupled to a CCD camera (T.I.L.L. photonics, Martinsried, Germany). Excitation light (552, 488 and 372 nm for Cy-3, FITC and DAPI, respectively) was obtained from a Xenon lamp coupled to a monochromator (T.I.L.L. photonics, Martinsried, Germany). Digital images were acquired using appropriate filters and combined using the TILLvision software.

Molecules Detected in the Progenitor or Stem Cells of the Invention

Using the above approaches, the following expression profile of a number of cell markers has been established in an experiment for the cells established in this example (ADHLSC):

CD90 positive. CD90, or Thy-1, is a cell-surface protein, considered to be indicative of mesenchymal lineage.

CD44 positive. CD44 is a cell-adhesion molecule and is used to identify at least some types of mesenchymal stem cells (MSC).

Vimentin positive. Vimentin is a type III intermediate filament commonly detected in mesenchymal cells and fibroblasts.

Albumin positive. Albumin is a plasma protein produced and secreted by the liver. Within hepatocytes, albumin is usually found as a cytoplasmic protein.

CD29 positive. CD29, also known as integrin beta-1, is a transmembrane glycoprotein, also present in hepatic tissue, thought to form with integrin alpha a functional receptor complex involved in interaction with extracellular matrix.

CD73 positive. CD73 is an ecto 5'-nucleotidase considered to be a mesenchymal marker.

CD49b positive. CD49b is also called integrin alpha-2 or collagen receptor and is implicated in cell interaction with extracellular matrix.

HLA-ABC positive. HLA-ABC (human leukocyte antigens A, B & C) are major histocompatibility complex class I antigens forming membrane heterodimers.

Alpha-fetoprotein—low levels of expression. Alpha-fetoprotein is a protein expressed during development of primitive endoderm and throughout maturation, reflects endodermal lineage. High levels of alpha-fetoprotein expression usually reveals tumorigenic shunt.

Alpha-1 antitrypsin positive. Alpha-1 anti trypsin is a plasma protein synthesized by the liver.

Glucose 6-phosphatase (G6P) positive. G6P is a liver enzyme that hydrolyzes glucose 6-phosphate to glucose and inorganic phosphate, allowing glucose in the liver to enter the blood.

Cytochrome P450 1B1 (CYP1B1) positive. CYP1B1 is a dioxin inducible cytochrome responsible for the phase I metabolism of a wide range of structurally diverse substrates Cytochrome P450 3A4 (CYP3A4) positive. CYP3A4 is a crucial enzyme involved in the metabolism of xenobiotics.

Hepatocyte Nuclear Factor 4 (HNF-4) positive. HNF4, a nuclear receptor, is a transcription factor involved in the regulation of energy metabolism.

Tryptophan 2,3-dioxygenase (TDO) positive. TDO is the first enzyme involved in tryptophan oxidation in the liver.

Tyrosine aminotransferase (TAT) positive. TAT is a mitochondrial liver specific enzyme involved in amino acid metabolism and gluconeogenesis Glutamine synthase (GS) positive. GS is a key enzyme for ammonium assimilation.

Gamma glutamyl transpeptidase (GGT) positive. GGT is an enzyme involved in the metabolism of glutathione.

Cytokeratin 8 (CK8) positive. CK8 is an intermediate filament specific of epithelial cells.

Multi-drug resistant protein 2 (MRP2) positive. MRP2 is an organ anion transporter responsible for the export of intracellular organic anions from hepatocytes to the biliary tree.

Glutamate transporter 2 (EAAT2) positive.

The presence of the above many molecules that may participate in liver function and metabolism is indicative of the close link of the ADHLSC cell line to liver phenotypes.

CD117 negative. CD117, also called c-kit, is a cell-surface receptor on bone marrow cell types that identifies HSC and MSC therefore characterize quite undifferentiated stem cells.

CD34 negative. CD34 is a cell surface protein on bone marrow cells, indicative of HSC and endothelial progenitor.

CD45 negative. CD45, also called leukocyte antigen, is a tyrosine phosphatase expressed cells of the hematopoietic lineage, including hematopoietic stem cells.

CD105 negative. CD105, also called SH2 or endoglin, is an adhesion molecule. It is also considered to be a marker of mesenchymal stem cells.

CD133 negative. CD133 is a hematopoietic stem cell marker.

HLA-DR negative. These major histocompatibility complex class II antigens are membrane heterodimers restrictively expressed in antigen presenting cells.

Oct-4 negative. Oct-4 is a transcription factor expressed only by pluripotent stem cells and essential for maintenance of the undifferentiated state.

Cytokeratin 19 (CK19) negative. CK19 is widely used as a marker for biliary cells, i.e., cholangiocytes.

Cytochrome P 2B6 (CYP2B6) negative. CYP2B6 is involved in the metabolism of endo- and xenobiotics.

CD54: Intercellular Adhesion Molecule-1 (ICAM-1), a membrane glycoprotein

Without intending to be limiting in any way, the present inventors, based on their knowledge of cell markers, put forward a following possible interpretation of the above data: This combination of markers defines an original cell line, which expresses markers from the mesenchymal lineage (CD90, CD73, vimentin, CD44) as well as markers characteristic of the hepatic differentiation path (CD29 and albumin, alpha-1 antitrypsin, HNF4, MRP2 transporter). The presence of albumin detected by both immuno-fluorescence and RT-PCR strongly argue against a possible contamination with stellate cells. The ADHLSC seem not to be pluripotent undifferentiated mesenchymal stem cells (CD45 negative, CD34 negative, CD117 negative, Oct-4 negative), nor liver stellate cells (albumin positive). The ADHLSC line seems committed to the hepatic lineage (CD29 positive, expressing albumin and alpha-1 anti trypsin) but does not express typical biliary marker (CK19 and 7 negative). Hence, the cells and cell lines of the invention may, in one and not limiting way, be denoted as mesenchymal stem cell line with characteristics of a hepatocyte progenitor.

uPA-SCID Mice Transplantation, Histology & Immunohistochemistry

One million ADHLSC (≥90% viability) were injected into the spleen of 6- to 14-day-old uPA$^{+/+}$-SCID mice. Before transplantation, mice showed undetectable serum albumin. Immunohistochemistry in mice liver samples was performed on four μm-thick liver sections that were stained with hematoxylin and eosin (HE) for overall histopathological evaluation. For immunostaining, liver slides were incubated overnight with primary antibodies at room temperature. Detection was performed after incubating the slices with peroxidase labeled polymer and substrate chromogen (Envision-DAB system, Dako, Carpinteria, Calif.). Counterstaining was performed using Hematoxylin.

The transgenic mouse model utilized for the purpose combines a liver pathology (uPA) with immunodeficiency (SCID). After intrasplenic transplantation of the ADHLSC suspension, the uPA$^{+/+}$-SCID mice were left to recover for 10 weeks. The analysis of the livers of uPA/SCID mice transplanted with ADHLSC, demonstrated that these cells were able to engraft (FIG. 4) and to differentiate into mature hepatocytes (FIG. 5). Furthermore, human albumin was detected in the serum of these transplanted mice 10 weeks post-transplantation whereas the level of expressed alpha-fetoprotein, a marker of tumour development, stayed untraceable.

The transplanted cells did not over-proliferate as shown by microscopic observation indicating the absence of tumorigenic colonies and normal level of expression of the tumorigenic markers alpha-fetoprotein and Ki67. The normal level of expression corresponds essentially to the level of expression measured in normal hepatocytes and less than the level of expression measured in the tumorigenic modified human liver cell line, e.g., HepG2.

EXAMPLE 2

An exemplary treatment with the liver originated progenitor or stem cells of the invention, cell lines thereof or cell populations comprising such (specifically mentioning, albeit of course not limited to, the LMBP 6452CB line), or progeny thereof, optionally genetically modified, may be as follows.

Cells are infused in serial injections, preferably not exceeding 25 to 50×10$^6$ cell/kg, preferably 4 hours apart, or 8 hrs apart, or more than 8 hrs up to one week, or more than one week. A total cell quantity of 250×10$^6$ cell/kg, or 500×10$^6$ cell/kg are infused over few days, preferably one or preferably two weeks. Serial infusions can be repeated as required, every month, or every six months, or every year or more.

Access to the portal vein is by direct puncture under radiological and or ultrasound guidance, via a puncture needle, or via a percutaneous catheter, or via a Port-a-cath R device, or via a Broviac R device inserted surgically in any vessel draining to the portal vein, preferably the inferior mesenteric vein, or a colonic vein. The catheter can be left in place for several hours, preferably several days, preferably several weeks, or preferably several months up to two years, or preferably longer for repeating infusions whenever needed.

Immunosuppression is started the day of infusion, preferably the day before, preferably with Tacrolimus (FK506) and steroids. Through blood level of Tacrolimus is preferably 8 ng/ml initially, 6 ng/ml after three months, 4 ng/ml after 6 months, then kept around 4 ng/ml. Steroids are preferably given as prednisone or prednisolone, initially 5 mg/kg at day 1, 4 mg/kg at day 2, 3 mg/kg at day 3, 2 mg/kg at day 4, 1 mg/kg at day 5, and then progressively decreased to reach 0.25 mg/kg at 3 months, and stop at six months. Alternative immunosuppression may include, alone or in combination, Ciclosporin A, anti IL2 receptor antibodies, anti thymocyte globulins, or any anti human lymphocyte monoclonal or polyclonal antibodies, mycophenolate mofetyl or azathioprine or any antimetabolite agent, ciclosporin, rapamune or any other calcineurin inhibitor.

What is claimed is:

1. An isolated human progenitor or stem cell originated from human adult liver characterized in that:
    (a) the isolated human progenitor or stem cell expresses at least the mesenchymal markers vimentin and α-smooth muscle actin (ASMA),
    (b) the isolated human progenitor or stem cell expresses the hepatocyte marker albumin (ALB),
    (c) the isolated human progenitor or stem cell is negative for cytokeratin-19 (CK-19), and
    (d) the isolated human progenitor or stem cell has mesenchymal-like morphology.

2. The isolated human progenitor or stem cell according to claim 1, further characterized in that the isolated human progenitor or stem cell expresses the markers CD90, CD73, and CD44.

3. The isolated human progenitor or stem cell according to claim 1, which further expresses one or more other hepatic or hepatocyte markers selected from CD29, alpha-fetoprotein (AFP), alpha-1 antitrypsin, HNF-4 and MRP2 transporter.

4. The isolated human progenitor or stem cell according to claim 3, which expresses CD29, AFP, alpha-1 antitrypsin and MRP2 transporter.

5. An isolated human progenitor or stem cell originated from human adult liver, which is CD90, CD29 and CD44 positive, and which is albumin-positive, vimentin-positive and alpha smooth muscle actin-positive, and which is negative for CD45, CD34, CD117 and CK-19.

6. The isolated human progenitor or stem cell according to claim 1, wherein the mesenchymal-like morphology involves any or all of growth in monolayers, flattened form, broad cytoplasm and ovoid nuclei with one or two nucleoli.

7. The isolated human progenitor or stem cell according to claim 1, wherein said cell can differentiate into hepatocytes or hepatocyte-like cells and does not differentiate into mesodermal cell types.

8. A cell line of or a cell population comprising the isolated human liver progenitor or stem cell according to claim 1, and progeny thereof.

9. An isolated human adult liver progenitor or stem cell, and cell line, as deposited on Feb. 20, 2006 under the Budapest Treaty with the Belgian Coordinated Collections of Microorganisms (BCCM) under accession number LMBP 6452CB, sub-lines thereof including clonal sub-lines, and progeny thereof.

10. A method for obtaining an isolated human progenitor or stem cell or a cell population comprising said progenitor or stem cell that expresses at least the mesenchymal markers vimentin and α-smooth muscle actin (ASMA), the hepatocyte marker albumin (ALB), is negative for cytokeratin-19 (CK-19), and has mesenchymal-like morphology, the method comprising:
   (a) disassociating human adult liver or a part thereof to form a population of primary cells from said adult liver or part thereof,
   (b) plating the primary cell population onto a substrate which allows adherence of cells thereto,
   (c) culturing cells from the primary cell population, which have adhered to said substrate, for at least 7 days in a culture medium comprising serum and a combination of at least two exogenously added growth factors selected from the group consisting of EGF, dexamethasone, and insulin, and
   (d) exchanging the medium for basal medium comprising high glucose at a concentration between 3000 mg/l and 6000 mg/l and further culturing the cells, whereby said progenitor or stem cell emerges and proliferates.

11. An isolated human adult liver progenitor or stem cell, cell line thereof and/or a cell population comprising such, obtainable by or directly obtained using the method of claim 10.

12. An isolated human adult liver progenitor or stem cell, cell line thereof and/or a cell population comprising such, according to claim 11, wherein the method comprises:
   (a) disassociating adult liver or a part thereof from a human subject, to form a population of primary cells from said adult liver or part thereof;
   (b) plating the primary cell population onto collagen type I coated substrate in Williams Medium E comprising foetal calf serum, EGF, insulin, and dexamethasone;
   (c) allowing adherence of cells from the primary cell population to said substrate for 24 hours and thereafter exchanging the medium for fresh medium having composition as in (b);
   (d) culturing the cells in said medium of (c) for 14-15 days;
   (e) exchanging the medium for DMEM comprising glucose at a concentration between 3000 mg/l and 6000 mg/l and FCS and further culturing the cells, whereby the progenitor or stem cells of the invention emerge and proliferate;
   (f) allowing the cells to become about 70% confluent and passaging the cells at least once, wherein the cells are plated onto the substrate as in (b) and cultured in a medium as in (e).

13. A composition comprising the human liver progenitor or stem cell according to claim 1.

14. The cell line or cell population of claim 8, or progeny thereof including differentiated progeny for use in therapy.

15. A method of treating liver disease comprising administering the human liver progenitor or stem cells according to claim 1 or progeny thereof to an individual in need thereof.

16. A pharmaceutical composition comprising the human liver progenitor or stem cell according to claim 1 and a pharmaceutically acceptable carrier.

17. A method for enhancing the regeneration of an injured or diseased liver comprising administering the human liver progenitor or stem cell according to claim 1 to an individual in need thereof.

18. A method for differentiation of human liver progenitor or stem cells or a cell population comprising said progenitor or stem cells to cells of hepatocyte lineage, particularly to hepatocytes or hepatocyte-like cells, comprising:
   obtaining human liver progenitor or stem cells or a cell population comprising said progenitor or stem cells by the method of claim 10; and
   exposing the progenitor or stem cells or the cell population comprising said progenitor or stem cells to liver differentiation-inducing medium.

* * * * *

UNITED STATES PATENT AND TRADEMARK OFFICE
CERTIFICATE OF CORRECTION

| | | |
|---|---|---|
| PATENT NO. | : 8,673,635 B2 | Page 1 of 1 |
| APPLICATION NO. | : 12/097743 | |
| DATED | : March 18, 2014 | |
| INVENTOR(S) | : Sokal et al. | |

It is certified that error appears in the above-identified patent and that said Letters Patent is hereby corrected as shown below:

On the Title Page

In column 1 (page 2, item 56) at line 26, Under Other Publications, change "Coves" to --Covas--.

In column 1 (page 2, item 56) at line 38, Under Other Publications, change "byBMP" to --by BMP--.

In the Specification

In column 7 at line 61, Change "100×" to --100×.--.

In column 8 at line 54, Change ""ex vivd"" to --"ex vivo"--.

In column 21 at lines 23-24, Change "Liebovitz" to --Leibovitz--.

In column 24 at line 53, Change "an" to --and--.

In column 35 at line 30, Change "arginosuccinate" to --argininosuccinate--.

In column 35 at line 30, Change "arigininosuccinate" to --argininosuccinate--.

In column 38 at line 16, Change "II," to --I,--. (first occurrence)

In column 38 at line 23, Change "non alcoholi steato hepatitis" to --nonalcoholic steatohepatitis--.

In column 39 at line 48, Change "immunoglobin" to --immunoglobulin--.

In column 44 at line 42, Change "invitrogen" to --Invitrogen--.

In column 46 at line 39, Change "substrates" to --substrates.--.

In column 47 at line 20, Change "glycoprotein" to --glycoprotein.--.

Signed and Sealed this
Thirtieth Day of September, 2014

Michelle K. Lee
*Deputy Director of the United States Patent and Trademark Office*